United States Patent [19]
Yatsunami et al.

[11] Patent Number: 5,153,203
[45] Date of Patent: Oct. 6, 1992

[54] QUINOLONE DERIVATIVES AND SALTS THEREOF, PREPARATION PROCESSES THEREOF, AND ANTIBACTERIAL AGENTS CONTAINING THE SAME

[75] Inventors: Takashi Yatsunami; Hitodshi Yamamoto; Yasuhiro Kuramoto; Norihiro Hayashi; Akira Yazaki; Satoshi Inoue; Shuichiro Noda; Hirotaka Amano, all of Takata, Japan

[73] Assignee: Wakunaga Seiyaku Kabushiki Kaisha, Osaka, Japan

[21] Appl. No.: 501,720

[22] Filed: Mar. 30, 1990

[30] Foreign Application Priority Data

Mar. 30, 1989 [JP] Japan ................................. 1-79523
Mar. 31, 1989 [JP] Japan ................................. 1-82322

[51] Int. Cl.$^5$ .................... A61K 31/47; C07D 401/10; C07D 401/12; C07D 413/10
[52] U.S. Cl. .................... 514/312; 514/212; 514/228.8; 514/230.2; 514/233.5; 514/233.8; 514/300; 514/305; 540/597; 544/96; 544/101; 544/362; 544/363; 546/123; 546/136; 546/156
[58] Field of Search ................. 546/156, 136; 514/312, 514/212, 305, 228.8; 544/96; 540/597

[56] References Cited

U.S. PATENT DOCUMENTS 4,473,568 9/1984 Hutt ..................... 424/246
4,956,465 9/1990 Schriewer et al. .......... 546/156

FOREIGN PATENT DOCUMENTS 339406 11/1989 European Pat. Off. .

OTHER PUBLICATIONS

Hirai et al., Chemical Abstracts, vol. 113, No. 78184 (1990) (Abstract for JP 69478 Mar. 8, 1990).
Ziegler et la., Chemical Abstracts, vol. 112, No. 158016 (1990) (Abstract for J. Het. Chem. pp. 1141–1145, Apr. 1989).
Eoguet Ambros et al., Chemical Abstracts, vol. 111, No. 174004 (1989) (Abstract for ES 2003196, Oct. 16, 1988).
Ito et al., Chemical Abstracts, vol. 106, No. 67134 (1987) (Abstract of JP 61/218586 Sep. 29, 1986).
J. Heterocyclic Chem., (1989), 26, "Synthesis and Antibacterial Activity of Some 7-Substituted 1-Ethyl-6-Fluoro-1,4-Dihydro-4-... ", Ziegler et al.

Primary Examiner—Mukund J. Shah
Assistant Examiner—E. Bernhardt
Attorney, Agent, or Firm—Oblon, Spivak, McClelland, Maier & Neustadt

[57] ABSTRACT

Antibacterial quinolone derivatives represented by the following formula and salts thereof are disclosed.

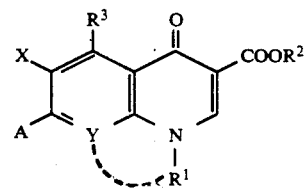

wherein $R^1$ means a substituted or unsubstituted lower alkyl group, a substituted or unsubstituted cycloalkyl group, a substituted or unsubstituted lower alkenyl group or a substituted or unsubstituted phenyl group, $R^2$ denotes a hydrogen atom or a carboxyl-protecting group, $R^3$ represents a hydrogen or halogen atom or an amino, mono- or di-(lower alkyl)amino, hydroxyl or lower alkoxyl group, X is a hydrogen or halogen atom, Y means a nitrogen atom or a group C-$R^4$ in which $R^4$ is a hydrogen or halogen atom or a lower alkyl or lower alkoxyl group or is a group

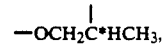

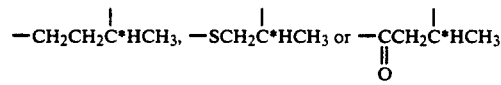

which forms a ring together with $R^1$ (i.e., the asterisked carbon atoms are linked to the N(1) atom of the quinolone skeleton), and A denotes a specific N-containing group. Preparation processes of the quinolone derivatives and antibacterial agents containing the same are also disclosed.

6 Claims, No Drawings

QUINOLONE DERIVATIVES AND SALTS THEREOF, PREPARATION PROCESSES THEREOF, AND ANTIBACTERIAL AGENTS CONTAINING THE SAME

BACKGROUND OF THE INVENTION

1) Field of the Invention

The present invention relates to novel quinolone derivatives and salts thereof, which are useful as synthetic antibacterial agents, to preparation processes thereof and also to antibacterial agents containing the same.

2) Description of the Related Art

Many of compounds having pyridonecarboxylic acid as a basic skeleton are known to be useful as synthetic antibacterial agents for their excellent antibacterial activities and broad antibacterial spectrum. Among these, norfloxacin [Japanese Patent Application Laid-Open (Kokai) No. 141286/1978], enoxacin [Japanese Patent Application Laid-Open (Kokai) No. 31042/1980], ofloxacin [Japanese Patent Application Laid-Open (Kokai) No. 46986/1982], ciprofloxacin [Japanese Patent Application Laid-Open (Kokai) No. 76667/1983] and the like have already found wide-spread clinical utility as therapeutic agents for infectious diseases.

Principal features of these compounds reside in that the quinoline skeleton or naphthyridine skeleton is substituted on position 6 with a fluorine atom and a secondary amino group is contained at position 7. In particular, the introduction of a piperazine ring or pyrrolidine ring to position 7 is considered to play a significant role in the enhancement of antibacterial activities.

However, these compounds are still not fully satisfactory in antibacterial activities, intestinal absorption, metabolic stability, or side effects, etc. There is an outstanding desire for the preparation of novel compounds which can satisfy these requirements.

SUMMARY OF THE INVENTION

With the foregoing in view, the present inventors have conducted an extensive investigation with a view toward providing clinically excellent synthetic antibacterial agents improved in the requirements described above. As a result, it has been found that compounds with a specific heterocyclic ring introduced on position 7 of the quinoline or naphthylidine skeleton can show superb antibacterial activities against gram-negative and gram-positive bacteria and can also satisfy other requirements and are hence useful as synthetic antibacterial agents, leading to the completion of the present invention.

The present invention therefore provides quinolone derivatives represented by the below-described formula [I] and salts thereof, their preparation processes and antibacterial agents containing them.

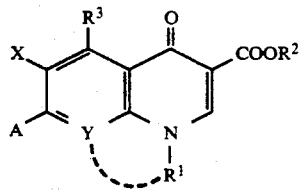

[I]

wherein $R^1$ means a substituted or unsubstituted lower alkyl group, a substituted or unsubstituted cycloalkyl group, a substituted or unsubstituted lower alkenyl group or a substituted or unsubstituted phenyl group, $R^2$ denotes a hydrogen atom or a carboxyl-protecting group, $R^3$ represents a hydrogen or halogen atom or an amino, mono- or di-(lower alkyl)amino, hydroxyl or lower alkoxyl group, X is a hydrogen or halogen atom, Y means a nitrogen atom or a group $C—R^4$ in which $R^4$ is a hydrogen or halogen atom or a lower alkyl or lower alkoxyl group or is a group

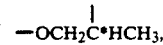

$$-OCH_2C^*HCH_3,$$

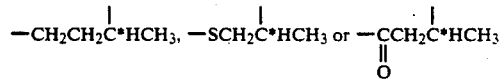

$$-CH_2CH_2C^*HCH_3, -SCH_2C^*HCH_3 \text{ or } -\underset{O}{\overset{\|}{C}}CH_2C^*HCH_3$$

which forms a ring together with $R^1$ (i.e., the asterisked carbon atoms are linked to the N(1) atom of the quinolone skeleton), A denotes a substituted or unsubstituted 3-oxazolidinyl group or a substituted or unsubstituted (tetrahydro-1,3-oxazin)-3-yl group or a group $-Z-(CH_2)_n-B$ in which Z is an oxygen atom or a group $N—R^5$, $R^5$ being a hydrogen atom, a lower group or a substituted or unsubstituted aralkyl group with the proviso that $R^1$ is other than an ethyl group when $R^5$ is a hydrogen atom, B represents a substituted or unsubstituted N-containing saturated heterocyclic group, and n stands for an integer of 0–2.

The compounds [I] and their salts according to the present invention are extremely valuable as antibacterial agents. They can therefore be used as drugs for human being and animals and also as drugs for fish diseases, agricultural chemicals and food preservatives.

DETAILED DESCRIPTION OF THE INVENTION AND PREFERRED EMBODIMENTS

In the present invention, the term "lower" employed in the definition for some substituent groups in formula [I] means that the group referred to has 1–7, preferably 1–5 carbon atoms when the substituent group is a linear or branched group but has 3–7 carbon atoms when the substituent group is a cyclic group.

Illustrative of the lower alkyl group represented by $R^1$ includes methyl, ethyl, isopropyl, t-butyl and t-pentyl. Examples of the substituted or unsubstituted lower alkyl group include those substituted by one or more halogen atoms or hydroxyl groups. Specific examples include 2-fluoroethyl, 2-hydroxyethyl and difluoromethyl. Exemplary substituted or unsubstituted alkenyl groups include vinyl, isopropenyl, allyl and 2-butenyl. Exemplary substituted or unsubstituted cycloalkyl groups include cyclopropyl, 1-methylcyclopropyl, cyclobutyl, cyclopentyl and cyclohexyl. Illustrative of the substituted or unsubstituted phenyl group include phenyl or phenyl groups substituted by one or more substituents such as halogen atoms, lower alkoxyl, lower acyloxy, hydroxyl, amino, lower alkyl and/or nitro groups. Specific examples include phenyl, 2-fluorophenyl, 4-fluorophenyl, 2,4-difluorophenyl, 2-hydroxyphenyl, 4-hydroxyphenyl, 2-methoxyphenyl, 4-methoxyphenyl, 2-fluoro-4-methoxyphenyl, 2-fluoro- 4-hydroxyphenyl, 4-methylphenyl, 4-acetyloxyphenyl, 4-aminophenyl and 4-nitrophenyl.

The term "carboxyl-protecting group" represented by $R^2$ indicates the ester residual group of a carboxylate ester and means a desired group capable of undergoing a relatively easy cleavage and yielding a corresponding free carboxyl group. Specific examples of the carboxyl-protecting group includes those removable upon treatment under mild conditions, such as hydrolysis or catalytic reduction, such as lower alkyl groups (e.g., methyl, ethyl, n-propyl, t-butyl, etc.), aralkyl groups (e.g., benzyl, etc.), and aryl groups (e.g., phenyl, etc.); and those readily removable in vivo, such as lower alkanoyloxy-lower alkyl groups (e.g., acetoxymethyl, pivaloyloxymethyl, etc.), lower alkoxycarbonyloxy-lower alkyl groups (e.g., methoxycarbonyloxymethyl, 1-ethoxycarbonyloxyethyl, etc.), lower alkoxymethyl groups (e.g., methoxymethyl, etc.), lactonyl groups (phthalidyl, etc.), di(lower alkyl)amino-lower alkyl groups (e.g., 1-dimethylaminoethyl, etc.), (5-methyl-2-oxol-4-yl)methyl group, and the like.

Illustrative of the halogen atom represented by $R^3$ include F, Cl and Br, with F and Cl being preferred. Examples of the lower alkoxyl group represented by $R^3$ include methoxy, ethoxy and isopropyloxy. Examples of the mono- or di-(lower alkyl)amino group represented by $R^3$ include methylamino, ethylamino and dimethylamino. Exemplary halogen atoms indicated by X include those exemplified as $R^3$, preferably F and Cl, and more preferably F.

Illustrative of the halogen atom represented by $R^4$ when Y is C—$R^4$ include F, Cl and Br, with F and Cl being preferred. Exemplary lower alkyl groups represented by $R^4$ include linear or branched alkyl groups having 1–4 carbon atoms, for example, methyl, ethyl, n-propyl, isopropyl and t-butyl. Illustrative of the lower alkoxyl group indicated by $R^4$ include those referred to above as $R^3$.

In the group —Z—$(CH_2)_n$—B represented by A, Z means an oxygen atom or N—$R^5$. Illustrative of the lower alkyl group represented by $R^5$ include those mentioned above with respect to $R^4$. Illustrative of the substituted aralkyl group includes benzyl. Further, illustrative the nitrogen-containing saturated heterocyclic group indicated by B include the following groups:

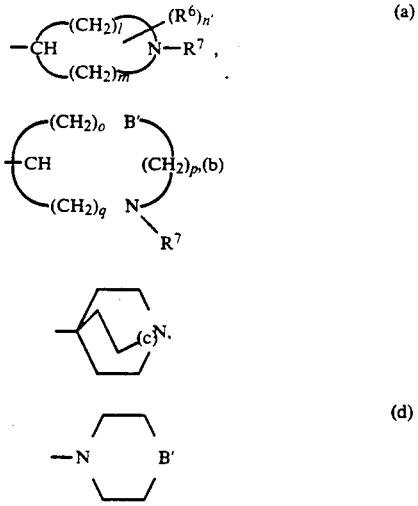

wherein B' means an oxygen or sulfur atom or N—$R^8$, n' groups of $R^6$ may be the same or different and individually mean a hydrogen atom or a lower alkyl group; $R^7$ and $R^8$ may be the same or different and individually denote a hydrogen atom, a substituted or unsubstituted lower alkyl group, a cyclo-lower alkyl group, a substituted or unsubstituted aralkyl group, a substituted or unsubstituted alkoxycarbonyl group, a substituted or unsubstituted acyl group, or an imidoyl group; and l stands for an integer of 1–3, m an integer of 1 or 2, n' an integer of 1–4, o an integer of 0 or 1, p an integer of 0–2, and q an integer of 0 or 1.

Preferred saturated heterocyclic groups indicated by the formula (a) include 2-azetidinyl, 3-azetidinyl, 2-pyrrolidinyl, 3-pyrrolidinyl, 2-piperidyl, 3-piperidyl and 4-piperidyl. Preferred saturated heterocyclic groups represented by the formula (b) include 2-thiazolidinyl, 4-thiazolidinyl, 5-thiazolidinyl, 2-oxazolidinyl, 4-oxazolidinyl, 5-oxazolidinyl, 2-imidazolidinyl, 4-imidazolidinyl, 3-pyrrazolidinyl, 2-morpholinyl, 3-morpholinyl, 2-thiomorpholinyl, 3-thiomorpholinyl, 2-piperadinyl and 3-piperadinyl.

Exemplary lower alkyl groups represented by $R^6$, $R^7$ and $R^8$ include methyl, ethyl, n-propyl, isopropyl and t-butyl. Illustrative of the substituted lower alkyl group indicated by $R^7$ and $R^8$ include lower alkyl groups substituted by one or more halogen atoms and/or hydroxyl, methoxy, amino, cyano, ethoxycarbonyl and/or carboxyl groups, for example, 2-hydroxyethyl, 2-methoxyethyl, 2-aminoethyl, 2-cyanoethyl, 2-ethoxycarbonylethyl, 2-fluoroethyl and 2-carboxymethyl. Exemplary cyclo-lower alkyl groups include cyclopropyl, cyclobutyl and cyclopentyl. Illustrative of the aralkyl group which may be substituted includes a benzyl group. Illustrative of the acyl group which may be substituted include acetyl, benzoyl and trifluoroacetyl. Exemplary alkoxylcarbonyl groups which may be substituted include ethoxycarbonyl, t-butoxycarbonyl and benzyloxycarbonyl. Exemplary imidoyl groups include formimidoyl, acetimidoyl and benzoimidoyl.

Illustrative of the substituent group on the 3-oxazolidinyl group or the (tetrahydro-1,3-oxazin)-3-yl group include lower alkyl groups (e.g., methyl, ethyl, n-propyl, isopropyl), hydroxy-lower alkyl groups (e.g., hydroxymethyl, hydroxyethyl), lower alkoxy-lower alkyl groups (e.g., methoxymethyl), amino-lower alkyl groups (e.g., aminomethyl, 1-aminoethyl, 2-aminoethyl), mono- or di(lower alkyl)aminolower alkyl groups (e.g., ethylaminomethyl, dimethylaminomethyl), hydroxyl group, lower alkoxy groups (e.g., methoxy, ethoxy, isopropyloxy), amino group, mono- or di-(lower alkyl)amino groups (e.g., methylamino, ethylamino, dimethylamino), etc.

Specific examples of the substituted 3-oxazolidinyl group include the following groups:

5-methyl-3-oxazolidinyl, 5-ethyl-3-oxazolidinyl, 5-propyl-3-oxazolidinyl, 5-hydroxymethyl-3-oxazolidinyl, 5-(1-hydroxyethyl)-3-oxazolidinyl, 5-(2-hydroxyethyl)-3oxazolidinyl, 5-methoxymethyl-3-oxazolidinyl, 5-ethoxymethyl-3-oxazolidinyl, 5-aminomethyl-3-oxazolidinyl, 5-(1-aminoethyl-3-oxazolidinyl, 5-(2-aminoethyl)-3-oxazolidinyl, 5-(1-aminopropyl)-3-oxazolidinyl, 5-(2-aminopropyl)-3oxazolidinyl, 5-(3-aminopropyl)-3-oxazolidinyl, 5-methylaminomethyl-3-oxazolidinyl, 5-dimethylaminomethyl-3oxazolidinyl, 5-(1-methylaminoethyl)-3-oxazolidinyl, 5-(2-methylaminoethyl)-3-oxazolidinyl, 5-(1-dimethylaminoethyl)-3-oxazolidinyl, 5-(2-dimethylaminoethyl)-3-oxazolidinyl, 5-ethylmethylaminomethyl-3-oxazolidinyl, 5-diethylaminomethyl- 3-oxazolidinyl, 4-methyl-3-oxazolidinyl, 2-methyl-3-oxazolidinyl, 4-methyl-5-hydroxymethyl-3-oxazolidinyl, 4-methyl-5-dimethylaminomethyl-3-oxazolidinyl, 2-methyl-5-aminomethyl-3-oxazolidinyl, and 2-methyl-5-ethylmethylaminomethyl-3-oxazolidinyl.

Specific examples of the substituted (tetrahydro-1,3-oxazin)-3-yl group include the following groups:

6-methyl-(tetrahydro-1,3-oxazin)-3-yl, 6-ethyl(tetrahydro-1,3-oxazin)-3-yl, 6-propyl-(tetrahydro-1,3-oxazin)-3-yl, 6-hydroxymethyl-(tetrahydro-1,3-oxazin)-3-yl, 6-(1-hydroxyethyl)-(tetrahydro-1,3-oxazin)-3-yl, 6-(2-hydroxyethyl)-(tetrahydro-1,3-oxazin)-3-yl, 6-methoxymethyl(tetrahydro-1,3-oxazin)-3-yl, 6-ethoxymethyl-(tetrahydro-1,3-oxazin)-3-yl, 6-aminomethyl-(tetrahydro-1,3-oxazin)-3-yl, 6-(1-aminoethyl)-tetrahydro-1,3-oxazin)-3-yl, 6-(2-aminoethyl)-tetrahydro-1,3-oxazin)-3-yl, 6-(1-aminopropyl)tetrahydro-1,3-oxazin)-3-yl, 6-(2-aminopropyl)-tetrahydro-1, 3-oxazin)-3-yl, 6-(3-aminopropyl)-(tetrahydro-1,3-oxazin)-3-yl, 6-methylaminomethyl-(tetrahydro-1,3-oxazin)-3-yl, 6-dimethylaminomethyl-(tetrahydro-1,3-oxazin)-3-yl, 6-(1-methylaminoethyl)-(tetrahydro-1,3-oxazin)-3-yl, 6-(2-methylaminoethyl)-(tetrahydro-1,3-oxazin)-3-yl, 6-(1-dimethylaminoethyl)-(tetrahydro-1,3-oxazin)-3-yl, 6-(2-dimethylaminoethyl)-(tetrahydro-1,3-oxazin)-3-yl, 6-ethylmethylaminomethyl-(tetrahydro-1,3-oxazin)-3-yl, 6-diethylaminomethyl-(tetrahydro- 1,3-oxazin)-3-yl, 5-methyl-(tetrahydro1,3-oxazin)-3-yl, 5-ethyl-(tetrahydro-1,3-oxazin)-3-yl, 5-propyl-(tetrahydro-1,3-oxazin)-3-yl, 5-hydroxymethyl-(tetrahydro-1,3-oxazin)-3-yl, 5-(1-hydroxyethyl)-(tetrahydro-1,3-oxazin)-3-yl, 5-(2-hydroxyethyl)-tetrahydro-1,3-oxazin)-3-yl, 5-methoxymethyl-(tetrahydro-1,3-oxazin-3-yl, 5-methoxymethyl-(tetrahydro-1,3-oxazin)-3-yl, 5-ethoxymethyl-(tetrahydro-1,3-oxazin)-3-yl, 5-aminomethyl-(tetrahydro-1,3-oxazin)-3-yl, 5-(1-aminoethyl)-(tetrahydro-1,3-oxazin)-3-yl, 5-(2-aminoethyl)-(tetrahydro-1,3-oxazin)-3-yl, 5-(1-aminopropyl)-(tetrahydro-1,3-oxazin)-3-yl, 5-(2-aminopropyl)(tetrahydro-1,3-oxazin)-3-yl, 5-(3-aminopropyl)-(tetrahydro1,3-oxazin)-3-yl, 5-methylaminomethyl-(tetrahydro-1,3-oxazin)-3-yl, 5-dimethylaminomethyl-(tetrahydro-1,3-oxazin)3-yl, 5-(1-methylaminoethyl)-(tetrahydro-1,3-oxazin)-3-yl, 5-(2-methylaminoethyl)-(tetrahydro-1,3-oxazin)-3-yl, 5-(1-dimethylaminoethyl)-(tetrahydro-1,3-oxazin)-3-yl, 5-(2-dimethylaminoethyl)-(tetrahydro-1,3-oxazin)-3-yl, 5-(ethylmethylaminomethyl)-(tetrahydro-1,3-oxazin)-3-yl, 5-diethylaminomethyl-(tetrahydro-1,3-oxazin)-3-yl, 4-methyl-(tetrahydro-1,3-oxazin)-3-yl, 2-methyl-(tetrahydro-1,3-oxazin)-3-yl, 5-hydroxy-(tetrahydro-1,3-oxazin)-3-yl, 5-methoxy(tetrahydro-1,3-oxazin)-3-yl, 5-ethoxy-(tetrahydro-1,3-oxazin)-3-yl, 5-amino-(tetrahydro-1,3-oxazin)-3-yl, 5-methylamino-(tetrahydro-1,3-oxazin)-3-yl, 5-dimethylamino(tetrahydro- 1,3-oxazin)-3-yl, 5-ethylamino-(tetrahydro-1,3-oxazin)-3-yl, 5-diethylamino-(tetrahydro-1,3-oxazin)-3-yl, 5-ethylmethylamino(tetrahydro-1,3-oxazin)-3-yl, 2-methyl-5-dimethylaminomethyl-(tetrahydro-1,3-oxazin)-3-yl, 2-methyl-6-methylamiomethyl-(tetrahydro-1,3-oxazin)-3-yl, 4-methyl-5-amino-(tetrahydro-1,3-oxazin)-3-yl, and 4-methyl-6-ethylmethylaminomethyl-(tetrahydro-1,3-oxazin)-3-yl.

The compounds [I] of the present invention can be converted into both acid addition salts and base addition salts. Exemplary acid addition salts include (a) the salts with mineral acids such as hydrochloric acid and sulfuric acid, (b) the salts with organic carboxylic acids such as formic acid, citric acid, trichloroacetic acid and trifluoroacetic acid, and (c) the salts with sulfonic acids such as methanesulfonic acid, benzenesulfonic acid, p-toluenesulfonic acid, mesitylenesulfonic acid and naphthalenesulfonic acid. On the other hand, illustrative base addition salts include (a) the salts with alkali metals such as sodium and potassium, (b) the salts with alkaline earth metals such as calcium and magnesium, (c) the ammonium salt, (d) the salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

The compounds [I] of the present invention may be not only in unsolvated forms but also in hydrated or solvated forms. The present invention therefore embraces the compounds [I] in any crystalline forms and their hydrated and solvated products.

Further, the compounds [I] of the present invention include those containing an asymmetric carbon atom in a substituent group on position 7. They can exist as optically active substances. These optically active substances are also embraced in the compounds of the present invention.

The compounds [I] of the present invention also include those containing two asymmetric carbon atoms in a substituent group on position 7. They can exist as different stereoisomers (cis-form, trans-form). These stereoisomers are also included in the compounds of the present invention.

Each compound [I] of the present invention can be prepared by a process suited for the types of its substituent groups. Preferred preparation processes are as follows:

Process 1

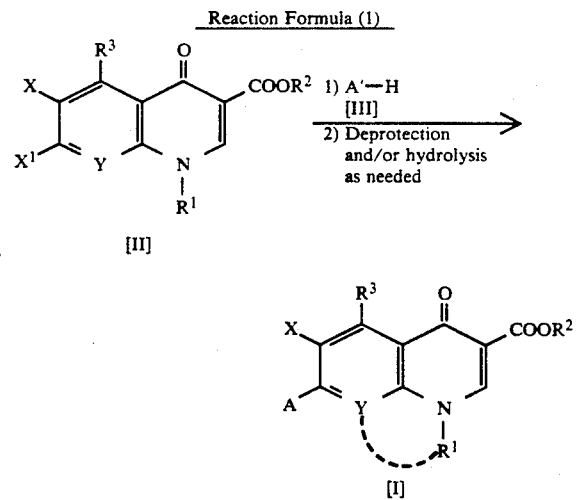

wherein $R^1$, $R^2$, $R^3$, X, Y and A have the same meanings as defined above, $X^1$ means a halogen atom, and A' denotes the same group as A or when the group A contains an amino, imino, hydroxyl or carboxyl group, the amino, imino, hydroxyl or carboxyl group may be protected.

Namely, the compound [I] of the present invention can be prepared by condensing the compound [II] and the compound [III] and if necessary, removing the protecting group and/or conducting hydrolysis.

The above condensation reaction is conducted in a solvent which does not give influence to the reaction, for example, an aromatic hydrocarbon such as benzene, toluene or xylene, an ether such as diethyl ether, tetrahydrofuran or monoglyme, a dipolar aprotic solvent such as dimethylformamide, dimethylsulfoxide, HMPA or sulfolane, acetonitrile, or pyridine, preferably in the presence of an acid-neutralizing agent, for example, a metal hydride such as sodium hydride or calcium hydride, an alkali metal such as sodium or potassium, an inorganic base such as sodium hydroxide, potassium hydroxide, sodium carbonate or potassium carbonate, or an organic base such as triethylamine, diisopropylethylamine or 1,8-diazabicyclo[5.4.0]undecene (DBU). This reaction proceeds normally at 0°–150° C., preferably about 0°–110° C. and is completed in 10 minutes to 24 hours or so. The compound [III] may be used in at least an equimolar amount, preferably in a molar amount 1–5 times relative to the compound [II].

When the compound [III] employed in the above reaction contains an amino, imino, hydroxyl or carboxyl group in the group A', the compound [III] may preferably be used in a form with such a group being protected, followed by the removal of the protecting group by a method known per as after completion of the reaction. Any protecting group can be used as long as it can be removed without destroying the structure of the compound of the present invention to be formed by the reaction. Protecting groups usually employed in the chemical field of peptides, aminosaccharides and nucleic acids can be used. Exemplary protecting groups for amino and imino groups include acetyl, t-butoxycarbonyl, benzyloxycarbonyl, trifluoroacetyl and benzyl. Illustrative protecting groups for a hydroxyl group include acetyl, benzoyl, benzyl and t-butyldimethylsilyl. Exemplary carboxylprotecting groups include those exemplified above.

When $R^2$ is a carboxyl-protecting group in the compound [I] obtained by the above reaction, the compound can be converted by usual hydrolysis, hydrogenolysis or the like into a compound in which $R^2$ is a hydrogen atom. The hydrolysis is conducted, for example, in the presence of a basic compound such as sodium hydroxide, potassium hydroxide, sodium carbonate or potassium carbonate, a mineral acid such as hydrochloric acid, sulfuric acid, hydrobromic acid, or an organic sulfonic acid such as p-toluenesulfonic acid; in a solvent, e.g., water, an alcohol such as methanol, ethanol or propanol, an ether such as tetrahydrofuran or dioxane, a ketone such as acetone or methyl ethyl ketone, or an organic acid such as acetic acid or propionic acid, or a mixed solvent thereof.

The starting compound [II] can be prepared by the process disclosed in any one of the following publications or by a similar process thereto:

1) J. Med. Chem., 23, 1358(1980)
2) J. Med. Chem., 27, 292(1984)
3) J. Med. Chem., 28, 1558(1985)
4) J. Med. Chem., 30, 504(1987)
5) J. Med. Chem , 29, 2363(1986)
6) Liebigs Ann. Chem., 29(1987)
7) Chem. Pharm. Bull., 34, 4098(1986)
8) J. Med. Chem., 31, 503(1988)
9) J. Med. Chem., 30, 465(1987)
10) Japanese Pat. Appln. Laid-Open (Kokai) No. 47658/1980
11) Japanese Pat. Appln. Laid-Open (Kokai) No. 30964/1981
12) Japanese Pat. Appln. Laid-Open (Kokai) No. 130594/1988
13) Japanese Pat. Appln. Laid-Open (Kokai) No. 145268/1988
14) Japanese Pat. Appln. Laid-Open (Kokai) No. 59263/1987
15) Japanese Pat. Appln. Laid-Open (Kokai) No. 277362/1987
16) Japanese Pat. Appln. Laid-Open (Kokai) No. 145268/1988
17) Japanese Pat. Appln. Laid-Open (Kokai) No. 187459/1987
18) Japanese Pat. Appln Laid-Open (Kokai) No. 264461/1988
19) Japanese Pat. Appln. Laid-Open (Kokai) No. 226962/1987
20) Japanese Pat. Appln. Laid-Open (Kokai) No. 228063/1987
21) Japanese Pat. Appln. Laid-Open (Kokai) No. 297366/1988
22) Japanese Pat. Appln. Laid-Open (Kokai) No. 28157/1990

Process 2

Among the compounds represented by the formula [I], those containing a carboxyl-protecting group as $R^2$ can be prepared, for example, by the reaction step shown by the following reaction formula (2).

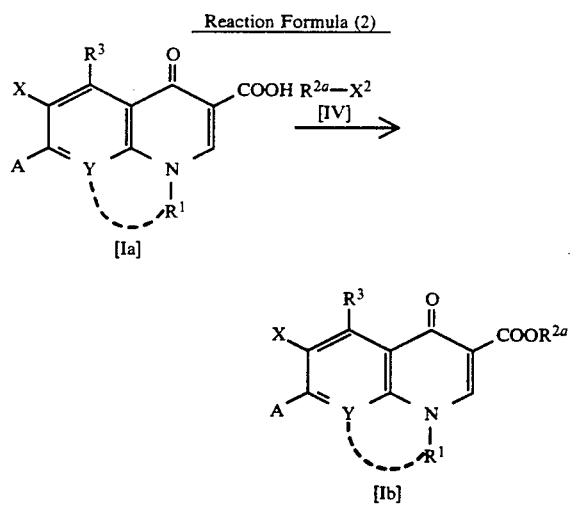

Reaction Formula (2)

wherein $R^1$, $R^3$, X, Y and A have the same meanings as defined above, $R^{2a}$ means a carboxyl-protecting group, and $X^2$ denotes a halogen atom.

The compound [Ib] can be obtained by reacting the halide [IV] with the compound [Ia]. Exemplary solvents usable in the reaction include inert solvents, for example, aromatic hydrocarbons such as benzene and toluene, halogenated hydrocarbons such as methylene chloride and chloroform, dipolar aprotic solvents such as dimethylformamide and dimethylsulfoxide, and ethers such as diethyl ether and tetrahydrofuran. The reaction temperature generally ranges from room temperature to about 100° C. Preferably, this reaction is carried out in the presence of a basic compounds such as triethylamine, diisopropylethylamine, dicyclohexylamine, DBU, sodium carbonate, potassium carbonate, sodium hydroxide or potassium hydroxide.

Process 3

Among the compounds of the present invention represented by the formula [I], those containing C—$R^4$ as y, $R^4$ being a lower alkoxy group, can be prepared, for example, by the reaction step shown by the following reaction formula (3).

Reaction Formula (3)

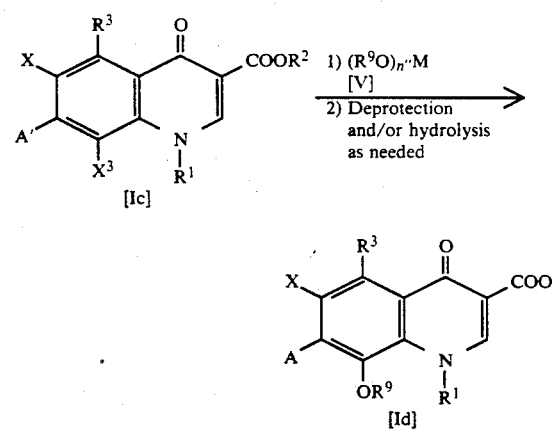

wherein $R^1$, $R^2$, $R^3$, X, A and A' have the same meanings as defined above, $X^3$ means a halogen atom, and $R^9$ denotes a lower alkyl group, M represents an alkali or alkaline earth metal atom, and n" stands for an integer of 1 or 2.

Namely, the compound [Id can be prepared by reacting the metal alkoxide [V with the compound [Ic]. Exemplary solvents useable in this reaction include those exemplified above under Process 1. This reaction proceeds normally at 0°–150° C., preferably about 0°–110° C. and is completed in 10 minutes to 24 hours or so. The compound [V may be used in at least an equimolar amount, preferably in a molar amount 1-5 times relative to the compound [Ic].

When an amino, imino, hydroxy or carboxyl group exists in the group A in the above reaction, it is preferably to use the compound [Ic] in a from with such a group being protected, followed by the removal of the protecting group by a method known per se after completion of the reaction.

When $R^2$ is a carboxyl-protecting group in the compound [I] obtained by the above reaction, the compound can be converted by usual hydrolysis or hydrogenolysis into a compound in which $R^2$ is a hydrogen atom. The hydrolysis is conducted under similar conditions to those described above under.

Process 1.

Process 4

Among the compounds represented by the formula [I], those containing an imidoyl as a substitutent in the group B can be prepared, for example, by the reaction step sown by the following reaction formula (4).

Reaction Formula (4)

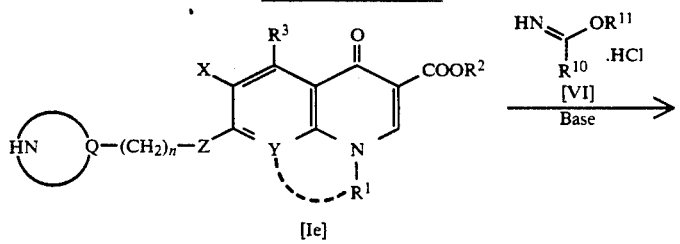

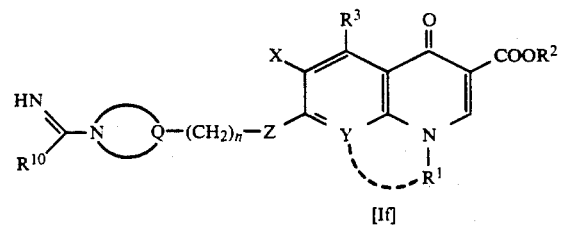

wherein $R^1$, $R^2$, $R^3$, X, Y, Z and n have the same meanings as defined above, $R^{10}$ means a hydrogen atom or a lower alkyl or aryl group, $R^{11}$ denotes a lower alkyl or substituted or unsubstituted aralkyl group, and

represents a substituted or unsubstituted divalent N-containing saturated heterocyclic group.

Namely, the compound [If] can be obtained by reacting the iminoether [VI] as hydrochloride with the compound [Ie] in the presence of an excess amount of a base. Exemplary solvents usable in the reaction include alcohols such as methanol, ethanol and n-propanol, dipolar aprotic solvents such as dimethylformamide, dimethylsulfoxide and HMPA, acetonitrile, and pyridine. Illustrative bases usable in the above reaction include organic bases such as triethylamine, diisopropylethylamine, DBU and pyridine, and inorganic bases such as sodium hydroxide, potassium hydroxide, sodium carbonate and potassium carbonate. The compound [VI] may be used in at least an equimolar amount, preferably in a molar amount 1-5 times relative to the compound [Ie]. This reaction proceeds at 0°–100° C., preferably about 0°–50° C. and is completed in 10 minutes to 10 hours or so. It is preferred to isolate the compound [If] in the form of a salt by adding an excess amount of an acid such as hydrochloric acid or hydrobromic acid after the completion of the reaction.

This reaction is preferably used when the group B is represented by the formula (a), (b) or (d).

Process 5

Among the compounds of the present invention represented by the formula [I], those containing a substituted or unsubstituted 3-oxazolidinyl group or a substituted or unsubstituted 3-oxazolidinyl group or a substituted or unsubstituted (tetrahydro-1,3-oxazin)-3-yl group as A, can be prepared, for example, by the reaction step shown by the following reaction formula (5).

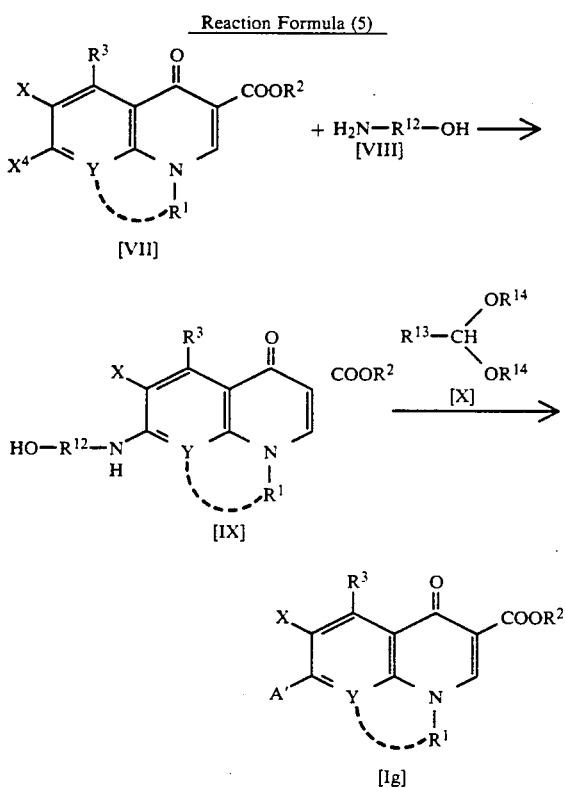

wherein $R^1$, $R^2$, $R^3$, X and Y have the same meanings as defined above, $X^4$ means a reactive leaving group, $R^{12}$ denotes a substituted or unsubstituted ethylene or substituted or unsubstituted propylene group, $R^{13}$ represents a hydrogen atom or a group capable of being converted to a substituted group on the 3-oxazolidinyl or the (tetrahydro-1,3-oxazin)-3-yl group as $A^1$, $R^{14}$ is a lower alkyl group, and $A^1$ means a substituted or unsubstituted 3-oxazolidinyl group or a substituted or unsubstituted (tetrahydro-1,3-oxazin)-3-yl group.

Namely, the compound [Ig] of the present invention can [VII] and the alkanolamine derivative [VIII] to obtain the compound [IX] and then reacting the dialkoxymethane derivative [X] with the compound [IX].

The reactive quinolone derivative [VII] can be prepared by any one of the processes described in the publications referred to above and the following publications and similar processes thereto.

1) J. Med. Chem., 27, 1103(1984)
2) Yakugaku Zasshi, 106, 802(1986)
3) Yakugaku Zasshi, 106, 795(1986)
4) J. Med. Chem., 29, 1531(1986)
5) Japanese Pat. Appln. Laid-Open (Kokai) No. 157068/1984
6) Japanese Pat. Appln. Laid-Open (Kokai) No. 212474/1984
7) Japanese Pat. Appln. Laid-Open (Kokai) No. 72885/1985
8) Japanese Pat. Appln. Laid-Open (Kokai) No. 260577/1985
9) Japanese Pat. Appln. Laid-Open (Kokai) No. 469/1987
10) Japanese Pat. Appln. Laid-Open (Kokai) No. 490/1987
11) Japanese Pat. Appln. Laid-Open (Kokai) No. 26272/1987
12) Japanese Pat. Appln. Laid-Open (Kokai) No. 53987/1987
13) Japanese Pat. Appln. Laid-Open (Kokai) No. 84085/1987
14) Japanese Pat. Appln. Laid-Open (Kokai) No. 155282/1987
15) Japanese Pat. Appln. Laid-Open (Kokai) No. 167768/1987
16) Japanese Pat. Appln. Laid-Open (Kokai) No. 174054/1987
17) Japanese Pat. Appln. Laid-Open (Kokai) No. 175482/1987
18) Japanese Pat. Appln. Laid-Open (Kokai) No. 175484/1987
19 Japanese Pat. Appln. Laid-Open (Kokai) No. 175485/1987
20) Japanese Pat. Appln. Laid-Open (Kokai) No. 187472/1987
21) Japanese pat. Appln. Laid-Open (Kokai) No. 187459/1987
22) Japanese Pat. Appln. Laid-Open (Kokai) No. 201869/1987
23) Japanese Pat. Appln. Laid-Open (Kokai) No. 205060/1987
24) Japanese Pat. Appln. Laid-Open (Kokai) No. 215572/1987
25) Japanese Pat. Appln. Laid-Open (Kokai) No. 226962/1987
26) Japanese Pat. Appln. Laid-Open (Kokai) No. 228063/1987
27) Japanese Pat. Appln. Laid-Open (Kokai) No. 39880/1988
28) Japanese Pat. Appln. Laid-Open (Kokai) No. 60990/1988

Illustrative of the reactive leaving group designated by $X^4$ in the formula [VII] include halogen atoms (e.g., F, I), arylsulfonyl groups (e.g., phenylsulfonyl), and arylsulfonyloxy groups (phenylsulfonyloxy).

The condensation reaction between the compound [VII] and the alkanolamine derivative [VIII] can be practiced by reacting them in an inert solvent and if necessary, in the presence of an acid-neutralizing agent, at 20°-160° C. for several minutes to several tens hours, preferably 10-24 hours.

Exemplary inert solvents usable in the above reaction include aromatic hydrocarbons such as benzene, toluene and xylene, alcohols such as methanol and ethanol, tetrahydrofuran, acetonitrile, pyridine, dimethylformamide, dimethylsulfoxide, and N-methylpyrrolidone. Illustrative of the acid-neutralizing agent include sodium carbonate, sodium hydrogencarbonate, potassium carbonate, triethylamine, and 1,8-diazabicyclo[5.4.0]-7-undecene.

When the starting compound [VIII] employed in the above reaction contains one or more amino groups which do not take part in the reaction, the starting compound is used in a form with the amino groups being protected. Any protecting groups can be used as long as they can be removed without destroying the structure of the compound of the present invention to be formed by the reaction. Protecting groups usually employed in the chemical field of peptides, aminosaccharides and nucleic acids can be used.

The reaction between the compound [IX] and the dialkoxymethane derivative [X] can be practiced by reacting them at 20°–160° C. under solventless conditions or in a solvent while using an acid catalyst.

Any solvent can be used in the reaction as long as it does not impede the reaction. Exemplary solvents include inert solvents, for example, aromatic hydrocarbons such as benzene, toluene and xylene, tetrahydrofuran, acetonitrile, dimethylformamide, and dimethylsulfoxide.

Illustrative of the acid catalyst includes mineral acids such as hydrochloric acid, hydrobromic acid, hydroiodic acid, sulfuric acid and phosphoric acid as well as organic acids such as acetic acid, citric acid and p-toluenesulfonic acid. Of these, p-toluenesulfonic acid is particularly preferred.

When the compound [IX] employed in the above reaction contains one or more amino and/or hydroxyl groups which do not take part in the reaction, the compound may be used in a form with the amino and/or hydroxyl groups being protected, followed by the removal of the protecting groups after the completion of the reaction. Any protecting groups can be used as long as they can be removed without destroying the structure of the compound of the present invention to be formed by the reaction. Protecting groups usually employed in the chemical field of peptides, aminosaccharides and nucleic acids can be used.

The thus-obtained compounds of the present invention can be isolated and purified by methods known per se in the art. They are obtained in the form of salts, carboxylic acid esters, free carboxylic acids or free amines, depending on the conditions for isolation and purification. However, they can be converted mutually from one of these forms into another one, whereby the compounds of the present invention can be prepared in a desired form.

Action (1) Antibacterial activities

With respect to certain representative compounds among the compounds [I] of the present invention, their minimum inhibitory concentrations (MIC; μg/ml) were measured in accordance with the standard method established by the Japan Society of Chemotherapy [CHEMOTHERAPY, 29(1), 76–79 (1981]. The results are summarized in Table 1, in which the compound numbers are as shown in examples.

TABLE 1

| Compound No. | Minimum inhibitory concentration (μg/ml) | | |
|---|---|---|---|
| | E. coli NIH JC-2 (IFO 12734) | S. aureus 209 P (IFO 12732) | P. aeruginosa (IFO 3445)* |
| 1 | 0.39 | 3.13 | 3.13 |
| 2 | 0.2 | 0.78 | 0.78 |
| 8 | 0.1 | 0.39 | 0.78 |
| 9 | 1.25 | 1.56 | 25.0 |
| 10 | 0.78 | 1.56 | 3.13 |
| 11 | 0.78 | 1.56 | 12.5 |
| 12 | 1.56 | 1.56 | 12.5 |
| 57 | 0.2 | 0.1 | 0.78 |
| 66 | 0.2 | 0.2 | 1.56 |
| 72 | 0.39 | 0.2 | 3.13 |

TABLE 1-continued

| Compound No. | Minimum inhibitory concentration (μg/ml) | | |
|---|---|---|---|
| | E. coli NIH JC-2 (IFO 12734) | S. aureus 209 P (IFO 12732) | P. aeruginosa (IFO 3445)* |
| 58 | 0.78 | 0.39 | 6.25 |
| 59 | 0.2 | 0.1 | 0.78 |
| 67 | 0.2 | 0.1 | 0.78 |
| 68 | 0.78 | 0.2 | 3.13 |
| 60 | 0.2 | 0.2 | 1.56 |
| 69 | 0.2 | 0.2 | 1.56 |
| 74 | 0.1 | 0.1 | 0.78 |
| 76 | 0.39 | 0.39 | 3.13 |

*IFO: Institute for Fermentation Osaka (2) Partition coefficient

Following the method proposed by Akira Tsuji et al. in Antimicrob. Agents Chemother., 32. 190–194 (1988), 50 mM phosphate buffer (pH 7.4, $\mu=0.15$)/n-octanol partition coefficients were measured. The measurement results of representative compounds are shown in Table 2.

TABLE 2

| Compound No. | Partition coefficient |
|---|---|
| 19 | 0.203 |
| 64 | 0.483 |

As has been described above, the compounds [I] and their salts according to the present invention are all novel compounds, exhibit extremely high antibacterial activities against gram-negative bacteria and gram-positive bacteria, and have high safety.

When the compounds [I] and their salts according to the present invention are used as antibacterial agents, they can be formulated into preparations along with a pharmaceutically-acceptable carrier for parenteral administration such as injection or rectal administration or for oral administration in the form of a solid or a liquid.

Preparations of this invention for use as injections can take the form of solutions, suspensions or emulsions in pharmaceutically-acceptable germ-free water or non-aqueous liquid. Exemplary suitable non-aqueous carriers, diluents, solvents and vehicles include propylene glycol, polyethylene glycol, vegetable oils such as olive oil, and injectable organic esters such as ethyl oleate. These preparations can contain one or more auxiliary agents, for example, antiseptics, wetting agents, emulsifiers and dispersants. These formulations can be sterilized, for example, by filtering them through a bacterial filter or by mixing, immediately before use, a sterilizing agent in the form of a germ-free solid composition soluble in sterilized water or one of some other media which can be sterilized and injected.

Exemplary solid preparations for oral administration include capsules, tablets, pills, powders, granules, etc. Upon formulation of these solid preparations, the compounds and their salts according to the present invention are generally mixed with at least one inert extender such as sucrose, lactose or starch. One or more materials other than inert extenders, for example, a lubricant such as magnesium stearate can also be incorporated in the preparations upon formulation of the latter in a usual manner. A buffer can also be incorporated in the case of capsules, tablets and pills. Tablets and pills can be applied with an enteric coating.

Illustrative liquid preparations includes pharmaceutically-acceptable emulsions, solutions, suspensions, syrups and elixirs, which contain an inert diluent employed commonly by those skilled in the art, for example, water. In addition to such an inert diluent, the liquid preparations can also be added with one or more auxiliary agents, for example, wetting agents, emulsifiers, suspending agents, sweetening agents, seasoning agents and perfumes.

Preparations for rectal administration are preferably suppositories which may contain an excipient such as cacao butter or suppository wax in addition to a compound or its salt according to the present invention.

The dosage of the compounds [I] and their salts according to the present invention generally ranges from about 0.1 mg/kg to 1,000 mg/kg per day, with about 1-100 mg/kg per day being preferred especially. If desired, this daily dosage can be administered in 2-4 portions.

The present invention will hereinafter be described by the following examples.

EXAMPLE 1

7-(3-Pyrrolidinyloxy)-1-cyclopropyl-6-fluoro-1,4-dihydro-4-oxoquinoline-3-carboxylic acid hydrochloride (Compound No. 1)

(1) To a mixture of 220 mg of ethyl 1-cyclopropyl-6,7-difluoro-1,4-dihydro-4-oxoquinoline-3-carboxylate, 280 mg of 1-t-butoxycarbonyl-3-hydroxypyrrolidine, 170 mg of DBU and 5 ml of DMF was added 65 mg of 55% sodium hydride while the former was stirred at room temperature. The resultant mixture was stirred for 2 hours at room temperature and then at 45° C. for 11 hours. The reaction mixture was concentrated to dryness under reduced pressure. Chloroform was added to the residue to dissolve the latter. The resultant solution was washed successively with a 10% aqueous solution of citric acid, a 5% aqueous solution of sodium hydrogencarbonate and saturated saline. The resulting chloroform layer was dried over anhydrous sodium sulfate and then concentrated. The residue was purified by chromatography on silica gel (chloroform/methanol: 100/1), whereby 140 mg of ethyl 7-(1-t-butoxycarbonyl-3-pyrrolidinyloxy)-1-cyclopropyl-6-fluoro1,4-dihydro-4-oxoquinoline-3-carboxylate was obtained.

$^1$H-NMR (CDCl$_3$) δ: 1.15–1.38(m,4H), 1.42(t,3H,J=8Hz), 1.48(s,9H), 2.10–2.40(m,2H), 3.35–3.75(m,5H), 4.38(q,2H,J=8Hz), 5.09(brs,1H), 7.35(d,1H,J=7Hz), 8.12(d,1H,J=12Hz), 8.53(s,1H).

(2) Ethyl 7-(1-t-butoxycarbonyl-3-pyrrolidinyloxy)-1-cyclopropyl-6-fluoro-1,4-dihydro-4-oxoquinoline-3carboxylate (210 mg) was dissolved in a mixture consisting of 0.7 ml of concentrated hydrochloric acid and 2.8 ml of acetic acid. The resulting solution was heated under reflux for 3 hours. The reaction mixture was concentrated to dryness under reduced pressure. The residue was recrystallized from ethanol, whereby 60 mg of the title compound was obtained as crystals.

Melting point: 266°–269° C. (decomposed).

$^1$H-NMR (DMSO-d$_6$) δ: 1.15–1.40(m,4H), 2.25–2.45(m,2H), 3.88(brs,1H), 5.58(brs,1H), 7.82(d,1H,J=7Hz), 8.08(d,1H,J=11Hz), 8.70(s,1H).

EXAMPLE 2

7-(3-Pyrrolidinyloxy)-1-cyclopropyl-6,8-difluoro-1,4-dihydro-4-oxoquinoline-3-carboxylic acid hydrochloride (Compound No. 2)

(1) To a mixture of 233 mg of ethyl 1-cyclopropyl-6,7,8-trifluoro-1,4-dihydro-4-oxoquinoline-3-carboxylate, 168 mg of 1-t-butoxycarbonyl-3-hydroxypyrrolidine, 170 mg of DBU and 5 xl of DMF was added 36 mg of 55% sodium hydride while the former was stirred at room temperature. After the resultant mixture was stirred for 1 hour at room temperature, the reaction mixture was concentrated to dryness under reduced pressure. After chloroform and 10% citric acid were added to the residue and the resultant mixture was shaken thoroughly, the resulting chloroform layer was collected and then successively washed with a 5% aqueous solution of sodium hydrogencarbonate and saturated saline. The chloroform solution was dried over anhydrous sodium sulfate and then concentrated. The residue was purified by chromatography on silica gel (chloroform/methanol: 100:1), whereby 210 mg of ethyl 7-(1-t-butoxycarbonyl-3-pyrrolidinyloxy)-1-cyclopropyl-6,8-difluoro-1,4-dihydro-4-oxoquinoline-3-carboxylate was obtained.

$^1$H-NMR (CDCl$_3$) δ:

1.02–1.35(m,4H), 1.40(t,3H,J=7Hz), 1.48(s,9H), 2.00–2.30(m,2H), 3.50–3.80(m,4H), 3.88(brs,1H), 4.38(q,2H,J=7Hz), 5.08(brs,1H), 8.03(d,1H,J=12Hz), 8.57(s,1H).

(2) Ethyl 7-(1-t-butoxycarbonyl-3-pyrrolidinyloxy)-1-cyclopropyl-6,8-difluoro-1,4-dihydro-4-oxoquinoline-3carboxylate (200 mg) was dissolved in a mixture consisting of 0.66 ml of concentrated hydrochloric acid and 2.66 ml of acetic acid. The resulting solution was heated under reflux for 3 hours. The reaction mixture was concentrated to dryness under reduced pressure. The residue was recrystallized from ethanol, whereby 74 mg of the title compound was obtained.

Melting point: 232°–237° C. (decomposed).

$^1$H-NMR (DMSO-d$_6$) δ: 1.10–1.35(m,4H), 2.05–2.35(m,2H), 4.15(brs,1H), 5.30(brs,1H), 8.05(d,1H,J=12Hz), 8.75(s,1H).

EXAMPLE 3

Compound Nos. 3–7 shown in Table 3 were obtained in a similar manner to Example 2.

TABLE 3

Structure: quinolone core with R2, F, A, Y substituents; N-R1; 3-COOH; 4-oxo

| Comp'd. No. | R¹ | R² | A | Y | Melting point (°C.) | Form | (Solvent) ¹H-NMR(δ) |
|---|---|---|---|---|---|---|---|
| 3 | cyclopropyl | H | 4-methoxy-1-methylpiperidine·HCl | CF | 218–222 | Colorless powder | (DMSO-$d_6$):<br>1.10–1.30(m, 4H), 2.20–2.35(m, 2H), 2.90(s, 3H), 4.12(brs, 1H), 5.28(brs, 1H), 8.03(d, 1H, J=12Hz), 8.73(s, 1H) |
| 4 | cyclopropyl | H | 3-(methoxymethyl)piperidine·HCl | CF | 141–146 | Colorless powder | (DMSO-$d_6$):<br>1.10–1.33(m, 4H), 1.72–1.88(m, 1H), 2.05–2.20 (m, 1H), 2.72–2.90(m, 1H), 3.00–3.30(m, 4H), 4.17(m, 1H), 4.30–4.45(m, 2H), 8.02(d, 1H, J=11Hz), 8.74(s, 1H) |
| 5 | cyclopropyl | H | 3-methoxypiperidine·HCl (3'R) form | CF | 247–250 | Colorless prism crystal (optically active) | (DMSO-$d_6$):<br>1.12–1.34(m, 4H), 2.05–2.30(m, 2H), 3.55(s, 2H), 4.16(m, 1H), 5.30(brs, 1H), 8.03(d, 1H, J=12Hz), 8.74(s, 1H) |
| 6 | cyclopropyl | H | 3-methoxypiperidine·HCl (3'S) form | CF | 247–251 | Colorless prism crystal (optically active) | (DMSO-$d_6$):<br>1.12–1.34(m, 4H), 2.05–2.35(m, 2H), 3.55(s, 2H), 4.16(m, 1H), 5.30(brs, 1H), 8.03(d, 1H, J=12Hz), 8.74(s, 1H) |
| 7 | cyclopropyl | H | 1-methoxy-quinuclidine·HCl | CF | 236–245 (decomposed) | Colorless prism crystal | (DMSO-$d_6$-$D_2O$):<br>1.10–1.30(m, 4H), 2.10–2.35(m, 6H), 3.30–3.60(m, 6H), 8.00(d, 1H, J=11Hz) 8.78(s, 1H) |

EXAMPLE 4

7-(3-Pyrrolidinyloxy)-1-cyclopropyl-5-amino-6,8-difluoro-1,4-dihydro-4-oxoquinoline-3-carboxylic acid hydrochloride (Compound No. 8)

(1) To a mixture of 277 mg of ethyl 1-cyclopropyl-5-amino-6,7,8-trifluoro-1,4-dihydro-4-oxoquinoline-3-carboxylate, 318 mg of 1-t-butoxycarbonyl-3-hydroxypyrrolidine, 194 mg of DBU and 3 ml of DMSO was added 74 mg of 55% sodium hydride while the former was stirred at room temperature. After the resultant mixture was stirred for 1 hour at room temperature, the reaction mixture was diluted with chloroform and then successively washed with 10% citric acid and saturated saline. The organic layer was dried over anhydrous sodium sulfate and then concentrated to dryness. The residue was recrystallized from ethanol, whereby 120 mg of 7-(1-t-butoxycarbonyl-3-pyrrolidinyloxy)-1-cyclopropyl-5-amino-6,8-difluoro-1,4-dihydro-4-oxoquinoline-3-carboxylic acid was obtained.

¹H-NMR (CDCl$_3$) δ: 1.01–1.28(m,4H), 1.47(s,9H), 2.00–2.30(m,2H), 3.50–3.80(m,4H), 3.92(brs,1H), 5.14(brs,1H), 6.63(brs,2H), 8.69(s,1H).

The mother liquor of the recrystallization was concentrated and the residue was purified by chromatography on silica gel (chloroform/methanol: 100:1), whereby 110 mg of ethyl 7-(1-t-butoxycarbonyl-3-pyrrolidinyloxy)-5-amino-6,8-difluoro-1,4-dihydro-4-oxoquinoline-3-carboxylate was obtained.

$^1$H-NMR (CDCl$_3$) δ: 1.00–1.20(m,4H), 1.38(t,3H,J=7Hz), 1.48(s,9H), 3.35–3.70(m,4H), 3.82(brs,1H), 4.38(q,2H,J=7Hz), 5.07(brs,1H), 6.80(brs,2H), 8.41(s,1H).

(2) 7-(t-Butoxycarbonyl-3-pyrrolidinyloxy)-1-cyclopropyl-5-amino-6,8-difluoro-1,4-dihydro-4-oxoquinoline-3-carboxylic acid (105 mg), 0 5 ml of concentrated hydrochloric acid and 2 xl of acetic acid were used. The compound was treated in a similar manner to Example 1-(2) and recrystallized from ethanol, whereby 82 mg of the title compound was obtained.

Melting point: 269°–274° C. (decomposed).
$^1$H-NMR (DMSO-d$_6$) δ: 1.00–1.25(m,4H), 2.05–2.30(m.2H), 4.03(brs,1H), 5.24(brs,1H), 7.50(brs,2H), 8.56(s,1H).

Ethyl 7-(t-butoxycarbonyl-3-pyrrolidinyloxy)-1-cyclopropyl-5-amino-6,8-difluoro-1,4-dihydro-4-oxoquinoline-3carboxylate (105 mg) was similarly treated using 0.5 ml of concentrated hydrochloric acid and 2 ml of acetic acid, whereby 38 mg of the title product was obtained.

EXAMPLE 5

10-(3-Pyrrolidinyloxy)-9-fluoro-2,3-dihydro-3-methyl-7-oxo-7H-pyrido[1,2,3-de][1,4]-benzoxazine-6-carboxylic acid hydrochloride (Compound No. 9)

(1) To a mixture of 263 mg of ethyl 9,10-difluoro-2,3-dihydro-3-methyl-7-oxo-7H-pyrido[1,2,3-de][1,4]-benzoxazine6-carboxylate, 318 mg of 1-t-butoxycarbonyl-3-hydroxypyrrolidine, 194 mg of DBU and 3 ml of DMSO was added 74 mg of 55% sodium hydride while the former was stirred at room temperature for 2.5 hours. After the resultant mixture was stirred at room temperature, the reaction mixture was diluted with chloroform and then successively washed with 10% citric acid and saturated saline. The organic layer was dried over anhydrous sodium sulfate and then concentrated to dryness. The residue was purified by chromatography on silica gel (chloroform/methanol: 100/1), whereby 220 mg of ethyl 10-(1-t-butoxycarbonyl-3-pyrrolidinyloxy)-9-fluoro2,3-dihydro-3-methyl-7-oxo-7H-pyrido[1,2,3-de][1,4]-benzoxazine-6-carboxylate was obtained.

$^1$H-NMR (CDCl$_3$) δ: 1.40(t,3H,J=3Hz), 1.47(s,9H), 1.60(3H), 1.90–2.25(m,2H), 3.40–3.80(m,4H), 4.27–4.45(m,5H), 5.05(brs,1H), 7.80(d,1H,J=12Hz), 8.36(s,1H).

(2) Ethyl 10-(1-t-butoxycarbonyl-3-pyrrolidinyloxy)-9-fluoro-2,3-dihydro-3-methyl-7-oxo-7H-pyrido[1,2,-3de][1,4]-benzoxazine-6-carboxylate (120 mg), 0.6 ml of concentrated hydrochloric acid and 2.6 ml of acetic acid were used. The ester was treated in a similar manner to Example 1-(2) and recrystallized from ethanol, whereby 50 mg of the title compound was obtained.

Melting point: 256°–260° C. (decomposed).
$^1$H-NMR (DMSO-d$_6$) δ: 1.45(d,3H,J=8Hz), 2.00–2.27(m,2H), 4.47 and 4.65(ABq,each 1H,J=11Hz), 4.95–5.07(m,1H), 5.23(brs,1H), 7.77(d,1H,J=12Hz), 9.08(s,1H).

EXAMPLE 6

7-(3-Pyrrolidinyloxy)-1-(2,4-difluorophenyl)-6-fluoro-1,4-dihydro-4-oxo-1,8-naphthyridine-3-carboxylic acid hydrochloride (Compound No. 10)

(1) To a mixture of 325 mg of ethyl 1-(2,4-difluorophenyl)-6-fluoro-7-chloro-1,4-dihydro-4-oxo-1,8-naphthyridine-3-carboxylate, 325 mg of 1-t-butoxycarbonyl-3hydroxypyrrolidine, 194 mg of DBU and 3 ml of DMF was added 46 mg of 55% sodium hydride while the former was stirred at room temperature. After the resultant mixture was stirred for 1.5 hours at room temperature, the reaction mixture was treated in a similar manner to Example 1-(1), whereby 240 mg of ethyl 7-(1-t-butoxycarbonyl-3-pyrrolidinyloxy)-1-(2,4-difluorophenyl)-6-fluoro-1,4-dihydro-4-oxo-1,8-naphthyridine-3-carboxylate was obtained.

$^1$H-NMR (CDCl$_3$) δ: 1.40(t,3H,J=7Hz), 1.43(s,9H), 1.80–2.20(m,2H), 3.20– 3.60(m,4H), 4.39(q,2H,J=7Hz), 5.05(brs,1H), 7.00–7.50(m,3H), 8.33(d,1H,J=10Hz), 8.48(s,1H).

(2) Ethyl 7-(1-t-butoxycarbonyl-3-pyrrolidinyloxy)-1-(2,4-difluorophenyl)-6-fluoro-1,4-dihydro-4-oxo-1,8-naphthyridine-3-carboxylate (220 mg), 0.7 ml of concentrated hydrochloric acid and 2.8 ml of acetic acid were used. The ester was treated in a similar manner to Example 1-(2) and recrystallized from ethanol, whereby 80 mg of the title compound was obtained.

Melting point: 263°–267° C. (decomposed).
$^1$H-NMR (DMSO-d$_6$) δ: 1.98–2.20(m,2H), 5.15(brs,1H), 7.30–7.90(m,3H), 8.52(d,1H,J=11Hz), 9.03(s,1H).

EXAMPLE 7

7-(1-Methyl-4-piperidyloxy)-1-ethyl-6-fluoro-1,4-dihydro-4-oxoquinoline-3-carboxylic acid (Compound No. 11)

To a mixture of 280 mg of 6,7-difluoro-1-ethyl-1,4-dihydro-4-oxoquinoline-3-carboxylic acid, 345 mg of N-methyl-4-piperidinol and 4 ml of DMF was added 200 mg of 50% sodium hydride while the former was stirred under ice cooling. After the resultant mixture was stirred for 2 hours at room temperature, 260 mg of acetic acid was added, followed by the addition of chloroform and water. The resultant mixture was thoroughly shaken and mixed. The chloroform layer was collected, washed with water, and then dried over sodium sulfate. The solvent was distilled off under reduced pressure. A solid thus precipitated was collected by filtration, whereby 38 mg of the title compound was obtained.

Melting point: 268°–271° C.
$^1$H-NMR (DMSO-d$_6$) δ: 1.41(t,3H,J=7Hz), 2.03–2.36(m,4H), 2.75(s,3H), 4.64(2H,q,J=7Hz), 5.09–5.20(m,1H), 7.58(d,1H,J=7Hz), 8.08(d,1H,J=11Hz), 9.0(s,1H).

EXAMPLE 8

10-(1-Methyl-4-piperidyloxy)-9-fluoro-2,3-dihydro-3-methyl-7-oxo-7H-pyrido[1,2,3-de][1,4]-benzoxazine-6-carboxylic acid (Compound No. 12)

9,10-Difluoro-2,3-dihydro-3-methyl-7-oxo-7H-pyrido[1,2,3-de][1,4]-benzoxazine-6-carboxylic acid (280 mg) was reacted and treated in a similar manner to Example 7, whereby 38 mg of the title compound was obtained.

Melting point: 234°-238° C.
¹H-NMR (DMSO-d₆) δ: 1.45(d,3H,J=7Hz), 1.67-1.98(m,4H), 2.21(s,3H), 2.60-2.71(m.2H). 4.35-4.50(m,2H), 4.60-4.70(m,1H), 4.91-5.04(m,1H), 7.70(d,1H,J=11Hz), 9.03(s,1H).

EXAMPLE 9

7-(1-Methyl-4-piperidyloxy)-1-cyclopropyl-6-fluoro-1,4-dihydro-4-oxoquinoline-3-carboxylic acid (Compound No. 13)

To a mixture of 530 mg of 6,7-difluoro-1-cyclopropyl-1,4-dihydro-4-oxoquinoline-3-carboxylic acid, 690 mg of N-methyl-4-piperidinol and 8 ml of DMF was added 320 mg of 60% sodium hydride while the former was stirred under ice cooling. After the resultant mixture was stirred for 10 minutes at room temperature, 480 mg of acetic acid was added. DMF was distilled off under reduced pressure. To the residue was added 15 ml of n-hexane. The resultant mixture was thoroughly shaken and mixed. The supernatant was discarded. To the resultant precipitate was added 8 ml of ethanol, followed by stirring. A precipitate thus precipitated was collected by filtration, whereby 578 mg of the title compound was obtained.

Melting point: 265°-269° C.
¹H-NMR (DMSO-d₆) δ: 1.02-1.13(m,2H), 1.22-1.32(m,2H), 1.72-2.87(m,2H), 1.99-2.12(m,2H), 2.20(s,1H), 2.21-2.33(m,2H), 2.55-2.69(m2H), 3.68-3.80(m,1H), 4.70-4.81(m,1H), 7.68(d,1H,J=8Hz), 7.93(d,1H,J=12Hz), 8.62(s,1H).

EXAMPLE 10

Compound Nos. 14-22 shown in Table 4 were obtained in a similar manner to Example 9.

TABLE 4

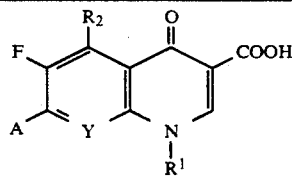

| Comp'd No. | R¹ | R² | A | Y | Melting point (°C.) | Form | (Solvent) ¹H-NMR(δ) |
|---|---|---|---|---|---|---|---|
| 14 | cyclopropyl | H | HN-piperidine-O- | CH | 213-217 | Colorless powder | (DMSO-d₆): 1.13-1.34(m, 4H), 1.54-1.68(m, 2H), 1.99-2.11 (m, 2H), 2.59-2.72(m, 2H), 2.94-3.06(m, 2H), 3.80-3.91(m, 1H), 4.80-4.90(m, 1H), 7.79 (d, 1H, J=7Hz), 8.00(d, 1H, J=11Hz), 8.68(s, 1H) |
| 15 | cyclopropyl | H | 3-methoxy-piperidine-NH | CH | 198-201 | Colorless powder | (DMSO-d₆): 1.12-1.36(m, 4H), 1.46-1.77(m, 3H), 2.10-2.21 (m, 1H), 2.46-2.85(m, 3H), 3.15-3.27(m, 1H), 3.81-3.91(m, 1H), 4.60-4.70(m, 1H), 7.79 (d, 1H, J=7Hz), 8.00(d, 1H, J=11Hz), 8.69(s, 1H) |
| 16 | cyclopropyl | H | 3-methoxy-N-methylpiperidine | CH | >300 | | (CDCl₃₂): 1.14-1.34(m, 2H), 1.34-1.45(m, 2H), 1.58-1.97 (m, 3H), 2.08-2.38(m, 3H), 2.36(s, 3H), 2.66-2.76 (m, 1H), 3.02-3.13(m, 1H), 3.50-3.60(m, 1H), 4.57-4.68(m, 1H), 7.58(d, 1H, J=7Hz), 8.12(d, 1H, J=11Hz), 8.80(s, 1H) |
| 17 | cyclopropyl | H | HN-piperidine-O- | CF | 228-231 | Colorless prism crystal | (DMSO-d₆): 1.13-1.26(m, 4H), 1.52-1.66(m, 2H), 1.88-2.00(m, 2H), 2.43-2.57(m, 2H), 2.92-3.05(m, 2H), 4.05-4.17 (m, 1H), 4.36-4.49(m, 1H), 7.96(d, 1H, J=11Hz), 8.68(s, 1H) |
| 18 | cyclopropyl | NH₂ | CH₃-N-piperidine-O- | CF | 219-222 | Pale green powder | (CDCl₃): 1.05-1.30(m, 4H), 1.88-2.07(m, 4H), 2.22-2.35 (m, 2H), 2.32(s, 3H), 2.66-2.79(m, 2H), 3.89-4.01(m, 1H), 4.42-4.53(m, 1H), 6.60 (brs, 1H), 8.72(s, 1H) |
| 19 | cyclopropyl | NH₂ | HN-piperidine-O- | CF | 218-223 (decomposed) | Pale brown powder | (DMSO-d₆): 1.05-1.28(m, 4H), 1.55-1.65(m, 2H), 1.87-1.98 (m, 2H), 2.45-2.57(m, 2H), 2.92-3.04(m, 2H), 3.97-4.09(m, 1H), 4.35-4.47(m, 1H), 7.43 (brs, 2H), 8.55(s, 1H) |
| 20 | cyclopropyl | H | CH₃-N-CH₃-N-azetidine-O- | CH | 209-213 | Pale brown powder | (CDCl₃): 1.18-1.28(m, 2H), 1.37-1.46(m, 2H), 2.56(s, 6H) 3.12-3.21(m, 2H), 3.27-3.35(m, 2H), 3.51-3.60 (m, 1H), 5.10-5.19(m, 1H), 7.42(d, 1H, J=7Hz), 8.11(d, 1H, J=11Hz), 8.80(s, 1H) |

TABLE 4-continued

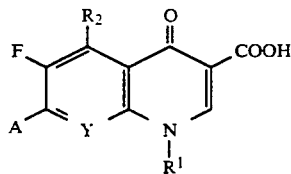

| Comp'd No. | R¹ | R² | A | Y | Melting point (°C.) | Form | (Solvent) ¹H-NMR(δ) |
|---|---|---|---|---|---|---|---|
| 21 | cyclopropyl | H | CH₃—N, CH₃—N (with ring)—O— | | 167–170 | Yellow powder | (CDCl₃): 1.15–1.38(m, 4H), 2.55(s, 6H), 3.17–3.27 (m, 4H), 3.96–4.05(m, 1H), 5.14–5.24(m, 1H), 8.04(dd, 1H, J=11Hz, 2Hz), 8.83(s, 1H) |
| 22 | cyclopropyl | NH₂ | pyrrolidine-N-CH₃ with —O— | | 211–214 | Pale green powder | (CDCl₃): 1.10–1.30(m, 4H), 2.05–2.38(m, 2H), 2.43(s, 3H), 2.45(m, 1H), 2.76–3.00(m, 3H), 3.94(m, 1H), 5.09(brs, 1H), 6.62(brs, 2H), 8.69(s, 1H) |

EXAMPLE 11

7-(1-Methyl-4-piperidyloxy)-1-cyclopropyl-6,8-difluoro-1,4-dihydro-4-oxoquinoline-3-carboxylic acid (Compound No. 23)

6,7,8-Trifluoro-1-cyclopropyl-1,4-dihydro-4-oxoquinoline-3-carboxylic acid (570 mg) was reacted in a similar manner to Example 9. Acetic acid (480 mg) was added and DMF was distilled off under reduced pressure. The residue was purified by columnchromatography on silica gel, whereby 160 mg of the title compound was obtained.

Melting point: 166°–167° C.

¹H-NMR (DMSO-d₆) δ: 1.12–1.31(m,4H), 1.70–2.07(m,4H), 2.18(s,3H), 2.57–2.72(m,2H), 4.10–4.23(m,1H), 4.37–4.50(m,1H), 7.98(d,1H,J=10Hz), 8.72(s,1H).

EXAMPLE 12

7-[(1-Methyl-3-pyrrolidinylmethyl)oxy]-1-cyclopropyl-5-amino-6,8-difluoro-1,4-dihydro-4-oxoquinoline-3-carboxylic acid (Compound No. 24)

To a mixture of 596 mg of 1-cyclopropyl-5-amino-6,7,8-trifluoro-1,4-dihydro-4-oxoquinoline-3-carboxylic acid, 460 mg of 1-methyl-3-hydroxymethylpyrrolidine and 5 ml of DMF was added 262 mg of 55% sodium hydride while the former was stirred at room temperature. After the resultant mixture was stirred for 1 hour at room temperature, 360 mg of acetic acid was added and DMF was distilled off under reduced pressure. The residue was purified by chromatography on silica gel (chloroform/methanol: 3/1), followed by recrystallization from ethanol. The title compound was obtained as pale green powder (yield: 240 mg).

Melting point: 193°–194° C.

¹H-NMR (CDCl₃) δ: 1.05–1.35(m,4H), 1.86(m,1H), 2.20(m,1H), 2.58(s,3H), 2.76–3.08(m,4H), 3.95(m1H), 4.28(brs.2H), 6.62(brs,2H), 8.68(s,1H).

EXAMPLE 13

(2′S)-7-[(2′-Pyrrolidinylmethyl)oxy]-1-cyclopropyl-6-fluoro-1,4-dihydro-4-oxoquinoline-3-carboxylic acid hydrochloride (Compound No. 25)

(1) To a mixture of 530 mg of 1-cyclopropyl-6,7-difluoro-1,4-dihydro-4-oxoquinoline-3-carboxylic acid, 1.20 g of 1-t-butoxycarbonyl-L-prolinol and 8 ml of DMF was added 200 mg of 55% sodium hydride while the former was stirred under ice cooling. The resultant mixture was stirred for further 15 minutes. The reaction mixture was poured into ice water and acidified with acetic acid. Crystals thus precipitated were collected by filtration. The thus-obtained crystals were dissolved in chloroform. The resultant solution was washed with water and then dried over anhydrous magnesium sulfate. Chloroform was distilled off. Crystals thus obtained were washed with diethyl ether and then dried, whereby 797 mg of (2′S)-7-[(1′-t-butoxycarbonyl-2′-pyrrolidinylmethyl)oxy]-1-cyclopropyl-6-fluoro-1,4-dihydro-4-oxoquinoline-3-carboxylic acid was obtained.

(2) To a 4N-hydrochloric acid/ethyl acetate solution was added 446 mg of (2′S)-7-[(1′-t-butoxycarbonyl-2′-pyrrolidinylmethyl)oxy]-1-cyclopropyl-6-fluoro-1,4-dihydro-4-oxoquinoline-3-carboxylic acid, followed by stirring for 1 hour at room temperature. After the reaction mixture was concentrated under reduced pressure, the residue was recrystallized from acetonitrile so that 370 mg of the title compound was obtained.

Melting point: 244°–247° C. (decomposed).

¹H-NMR (DMSO-d₆) δ: 1.19–1.40(m,4H), 1.82–2.23(m,4H), 3.25(m,2H), 3.87(m,1H), 4 06(m,1H), 4.61(m,2H), 7.84(d,1H,J=7Hz), 8.05(d,1H,J=11Hz), 8 72(s,1H).

EXAMPLE 14

Compound Nos. 26–35 shown in Table 5 were obtained in a similar manner to Example 13.

TABLE 5

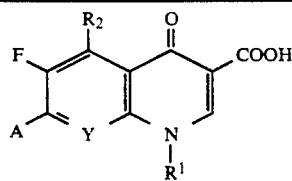

| Comp'd. No. | R¹ | R² | A | Y | Melting point (°C.) | Form | (Solvent) ¹H-NMR(δ) |
|---|---|---|---|---|---|---|---|
| 26 | cyclopropyl | $NH_2$ | (piperidine-$CH_2O$—·HCl) (2'S) form | CF | 241–244 (decomposed) | (optically active) | (DMSO-$d_6$): 1.13(m, 4H), 1.74–2.17(m, 4H), 3.22(m, 2H), 3.92–4.03(m, 2H), 4.57(m, 2H), 7.50(brs, 2H), 8.56(s, 1H), 9.22(brs, 2H), 9.70(brs) |
| 27 | cyclopropyl | H | (piperidine-$CH_2O$—·HCl) (2'S) form | CF | 198–200 | (optically active) | (DMSO-$d_6$): 1.19–1.26(m, 4H), 1.72–2.18(m, 4H), 3.24 (m, 2H), 2.96(m, 1H), 4.15(m, 1H), 4.64 (m, 2H), 8.00(dd, 1H, J=11Hz, 2Hz), 8.73(s, 1H), 9.75(brs, 2H), 9.51(brs, 1H), 9.86(brs, 1H) |
| 28 | cyclopropyl | H | (S-piperidine-$CH_2O$—·HCl) (3'R) form | CH | 204–206 | (optically active) | (DMSO-$d_6$): 1.22–1.41(m, 4H), 3.13(m, 1H), 3.41(m, 1H), 3.89(m, 1H), 4.32(m, 1H), 4.40(s, 2H), 4.71(m, 1H), 7.89(d, 1H, J=7Hz), 8.07(d, 1H, J=13Hz), 8.73(s, 1H) |
| 29 | cyclopropyl | $NH_2$ | (S-piperidine-$CH_2O$·HCl) (3'R) form | CF | | (optically active) | (DMSO-$d_6$): 1.16(m, 4H), 3.10(m, 1H), 3.35(m, 1H), 4.06(m, 1H), 4.19(m, 1H), 4.37(s, 2H), 4.63(m, 2H), 7.55(brs, 2H), 8.58(s, 1H) |
| 30 | cyclopropyl | H | ($H_3C$-piperidine-O—·HCl) (3'R, 5'R) form | CF | 231–233 | Colorless powder (optically active) | (DMSO-$d_6$): 1.18–1.30(m, 4H), 1.40(d, 3H, J=7Hz), 1.18–1.95 (m, 1H), 2.34–2.41(m, 1H), 3.48–3.56(m, 1H), 3.68–3.79(m, 1H), 3.83–3.92(m, 1H), 4.13–4.21(m, 1H), 5.28–5.32(m, 1H), 8.05(d, 1H, J=12Hz), 8.75(s, 1H) |
| 31 | cyclopropyl | H | ($H_3C$-piperidine-O—·HCl) (3'R, 5'R) form | CH | 249–253 (decomposed) | Colorless powder (optically active) | (DMSO-$d_6$): 1.18–1.24(m, 2H), 1.32–1.46(m, 5H), 2.01–2.10(m, 1H), 3.15–3.20(m, 1H), 3.58–3.62(m, 1H), 3.65–3.98 (m, 2H), 4.10–4.20(m, 1H), 5.60–5.70(m, 1H), 7.79(d, 1H, J=7Hz), 8.05(d, 1H, J=12Hz), 8.73(s, 1H) |
| 32 | cyclopropyl | $NH_2$ | ($H_3C$-piperidine-O—·HCl) (3'R, 5'R) form | CF | 236–239 (decomposed) | Brown powder (optically active) | (DMSO-$d_6$): 1.15(brs, 4H), 1.40(d, 3H, J=7Hz), 1.80–1.91(m, 1H), 2.33–2.40(m, 1H), 3.70–3.85(m, 2H), 4.05(m, 1H), 5.23(brs, 1H), 7.52(brs, 2H), 8.56(s, 1H) |

TABLE 5-continued

[Structure shown with R2, F, A, Y, N-R1, and COOH groups on quinolone core]

| Comp'd. No. | R¹ | R² | A | Y | Melting point (°C.) | Form | (Solvent) ¹H-NMR(δ) |
|---|---|---|---|---|---|---|---|
| 33 | cyclopropyl | H | piperidine-CH₂O— ·HCl (2'R) form | CF | 198–200 | Colorless powder (optically active) | (DMSO-d₆): 1.18–1.29(m, 4H), 1.72–2.18(m, 4H), 3.21–3.29(m, 2H), 3.93–4.02(m, 1H), 4.13–4.20(m, 1H), 4.30–4.40(m, 2H), 8.00(d, 1H, J=11Hz), 8.73(s, 1H) |
| 34 | cyclopropyl | H | piperidine-CH₂O— ·HCl (2'R) form | CH | 224–226 (decomposed) | Colorless needle crystal (optically active) | (DMSO-d₆): 1.19–1.40(m, 4H), 1.80–2.28(m, 4H), 3.20–3.28 (m, 2H), 3.81–3.92(m, 1H), 4.06(m, 1H) 4.61(m, 2H), 7.84(d, 1H, J=7Hz), 8.05(d, 1H, J=11Hz), 8.72(s, 1H) |
| 35 | cyclopropyl | NH₂ | piperidine-CH₂O— ·HCl (2'R) form | CF | 226–231 (decomposed) | Pale green powder (optically active) | (DMSO-d₆): 1.13(m, 4H), 1.72–2.21(m, 4H), 3.22(m, 2H), 3.86–4.12(m, 2H), 4.54–4.67(m, 2H), 7.51(brs, 2H), 8.56(s, 1H) |

EXAMPLE 15

7-[(1-Methyl-3-pyrrolidinylmethyl)oxy]-1-cyclopropyl-6-fluoro-1,4-dihydro-4-oxoquinoline-3-carboxylic acid hydrochloride (Compound No. 36)

To a mixture of 530 mg of 1-cyclopropyl-6,7-difluoro-1,4-dihydro-4-oxoquinoline-3-carboxylic acid, 460 mg of 1-methyl-3-hydroxymethylpyrrolidine and 5 ml of DMF was added 262 mg of 55% sodium hydride while the former was stirred at room temperature. After the resultant mixture was stirred for 1.5 hours at room temperature, 360 mg of acetic acid was added and DMF was then distilled off under reduced pressure. The residue was purified by chromatography on silica gel (chloroform/methanol: 3/1). Relevant fractions were dissolved in ethanol. To the solution was added 0.5 ml of a 4N-hydrochloric acid/dioxane solution. The resultant mixture was stirred and then concentrated under reduced pressure. The residue was recrystallized from ethanol-diisopropyl ether, whereby 66 mg of the title compound was obtained as colorless needle crystals.

Melting point: 214°–223° C.

¹H-NMR (DMSO-d₆) δ: 1.15–1.45(m,4H), 1.75–2.40(m,2H), 2.82(s,3H), 3.86(brs,1H), 4.46(brs,2H), 7.82(d,1H,J=8Hz), 8.03(d,1H,J=12Hz), 8.70(s,1H).

EXAMPLE 16

(3'R)-7-(3'-Pyrrolidinyloxy)-1-cyclopropyl-5-amino-6,8-difluoro-1,4-dihydro-4-oxoquinoline-3-carboxylic acid hydrochloride (Compound No. 37)

(1) To a mixture of 298 mg of 1-cyclopropyl-5-amino-6,7,8-trifluoro-1,4-dihydro-4-oxoquinoline-3-carboxylic acid, 374 mg of (3R)-1-t-butoxycarbonyl-3-hydroxypyrrolidine and 3 ml of DMF was added 120 mg of 55% sodium hydride while the former was stirred at room temperature. After the resultant mixture was stirred for 6 hours at room temperature, the reaction mixture was diluted with chloroform and then successively washed with 10% citric acid and saturated saline. The organic layer was dried over anhydrous sodium sulfate and concentrated to dryness. The residue was recrystallized from ethanol, whereby 326 mg of (3'R)-7-(1'-t-butoxycarbonyl-3'-pyrrolidinyloxy)-1-cyclopropyl-5-amino-6,8-difluoro-1,4-dihydro-4-oxoquinoline-3-carboxylic acid was obtained.

¹H-NMR (CDCl₃) δ:
1.10–1.30(m,4H), 1.50(s,9H), 1.90–2.35(m,2H), 3.50–3.83(m,4H), 3.92(m,1H), 5.15(brs,1H), 6.62(brs,2H), 8.70(s,1H).

(2) (3'R)-7-(1'-t-Butoxycarbonyl-3'-pyrrolidinyloxy)-1-cyclopropyl-5-amino-6,8-difluoro-1,4-dihydro-4-oxoquinoline-3-carboxylic acid (290 mg) was dissolved in a mixture which consisted of 1.25 ml of concentrated hydrochloric acid and 5 ml of acetic acid. The resultant mixture was heated under reflux for 1 hour. The reaction mixture was concentrated under reduced pressure. The residue was recrystallized from ethanol, whereby 214 mg of the title compound was obtained as pale green powder.

Melting point: 263°–267° C., (decomposed).

¹H-NMR (DMSO-d₆) δ: 1.05–1.20(m,4H), 2.05–2.30(m,2H), 3.53(m,2H), 4.05(m,1H), 5.25(brs,1H), 7.53(brs,2H), 8.58(s,1H).

EXAMPLE 17

Compound Nos. 38–40 shown in Table 6 were obtained in a similar manner to Example 16.

TABLE 6

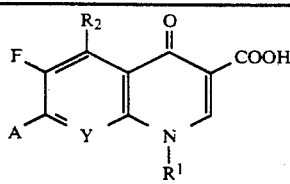

| Comp'd No. | R¹ | R² | A | Y | Melting point (°C.) | Form | (Solvent) ¹H-NMR(δ) |
|---|---|---|---|---|---|---|---|
| 38 | △ | NH₂ | (structure: pyrrolidine-O— ,,,,, ·HCl) (3'S) form | CF | 264–269 (decomposed) | Pale green powder (optically active) | (DMSO-d₆): 1.05–1.20(m, 4H), 2.05–2.30(m, 2H), 3.53(m, 2H), 4.05(m, 1H), 5.25(brs, 1H), 5.25(brs, 1H), 7.50(brs, 2H), 8.58(s, 1H) |
| 39 | △ | NH₂ | (structure: piperidine with CH₂O— ·HCl) | CF | 252–254 (decomposed) | Pale green powder | (DMSO-d₆): 1.00–1.20(m, 4H), 1.70–1.87(m, 1H), 2.03–2.20 (m, 1H), 2.68–2.85(m, 1H), 2.95–3.25(m, 4H), 4.03(m, 1H), 4.25–4.42(m, 2H), 7.48(brs, 2H), 8.54(s, 1H) |
| 40 | △ | NH₂ | (structure: HN-azetidine-O— ·HCl) | CF | 219–221 (decomposed) | Pale green prism crystal | (DMSO-d₆): 1.05–1.25(m, 4H), 4.02(brs, 1H), 4.10–4.45 (m, 4H), 5.26(brs, 1H), 7.52(brs, 2H), 8.55(s, 1H) |

EXAMPLE 18

7-(1-t-Butoxycarbonyl-3-pyrrolidinyloxy)-1-cyclopropyl-6,8-difluoro-1,4-dihydro-4-oxoquinoline-3-carboxylic acid (Compound No. 41)

A mixture of 1.28 g of ethyl 7-(1-t-butoxycarbonyl-3-pyrrolidinyloxy)-1-cyclopropyl-6,8-difluoro-1,4-dihydro-4-oxoquinoline-3-carboxylate, 3.5 ml of 1N aq. sodium hydroxide solution and 30 ml of tetrahydrofuran was heated under reflux for 1.5 hours. The mixture was concentrated under reduced pressure. To the residue was added 10% aq. citric acid to acidify the same, followed by extraction with chloroform. The chloroform layer was washed with saturated saline, dried over anhydrous sodium sulfate, and then concentrated to dryness. The residue was recrystallized from chloroform-diisopropyl ether, whereby 1.11 g of the title compound was obtained as colorless powder.

Melting point: 158°–160° C.

¹H-NMR (CDCl₃) δ: 1.15–1.40(m,4H), 1.47(s,9H), 1.97–2.35(m,2H), 3.50–3.80(m,4H), 3.98(m,1H), 5.16(brs,1H), 8.04(d,1H,J=12Hz), 8.83(s,1H).

EXAMPLE 19

7-(1-t-Butoxycarbonyl-3-pyridinyloxy)-1-cyclopropyl-5-amino-6,8-difluoro-1,4-dihydro-4-oxoquinoline-3-carboxylic acid (Compound No. 42)

To a mixture of 1.20 g of 1-cyclopropyl-5-amino-6,7,8-trifluoro-1,4-dihydro-4-oxoquinoline-3-carboxylic acid, 1.50 g of 1-t-butoxycarbonyl-3-hydroxypyrrolidine and 1.5 ml of DMF was added 483 mg of 55% sodium hydride while the former was stirred under ice cooling. The resultant mixture was stirred for further 20 hours at room temperature. The reaction mixture was diluted with chloroform and then successively washed with 10% aq. citric acid solution and saturated saline. The organic layer was dried over anhydrous sodium sulfate and then concentrated. The residue thus obtained was recrystallized from ethanol, whereby 1.48 g of the title compound was obtained as pale green powder.

Melting point: 208°–212° C.

¹H-NMR (CDCl₃) δ: 1.10–1.30(m,4H), 1.50(s,9H), 1.90–2.35(m,2H), 3.50–3.83(m,4H), 3.92(m,1H), 5.15(brs,1H), 6.62(brs,2H), 8.70(s,1H).

EXAMPLE 20

7-(3-Pyrrolidinyloxy)-1-cyclopropyl-6-fluoro-8-methoxy-1,4--dihydro-4-oxoquinoline-3-carboxylic acid hydrochloride (Compound No. 43)

(1) 7-(1-t-Butoxycarbonyl-3-pyrrolidinyloxy)-1-cyclopropyl-6,8-difluoro-1,4-dihydro-4-oxoquinoline-3-carboxylic acid (300 mg) was dissolved in 3 ml of DMF, followed by the addition of 32 mg of 55% sodium hydride under ice cooling. After the resultant mixture was stirred for 10 minutes, 72 mg of sodium methoxide was added. The mixture thus obtained was stirred further for 18 hours at room temperature. The reaction mixture was diluted with chloroform and then washed successively with 10% aq. citric acid solution and saturated saline. The organic layer was dried over anhydrous sodium sulfate and then concentrated to dryness, whereby 7-(1-t-butoxycarbonyl-3-pyrrolidinyloxy)-1-cyclopropyl-6-fluoro-8-methoxy-1,4-dihydro-4-oxoquinoline-3-carboxylic acid was obtained. It was used directly in the reaction of the next step without further purification.

¹H-NMR (CDCl₃) δ: 1.05–1.30(m,4H), 1.50(s,9H), 2.00–2.30(m,2H), 3.50–3.85(m,4H), 3.98(s,3H), 4.10(m,1H), 5.11(brs,1H), 8.01(d,1H,J=12Hz), 8.86(s,1H).

(2) The whole amount of the 7-(1-t-butoxycarbonyl-3-pyrrolidinyloxy)-1-cyclopropyl-6-fluoro-8-methoxy-1,4-dihydro-4-oxoquinoline-3-carboxylic acid obtained above was dissolved in a mixture which consisted of 1.25 ml of concentrated hydrochloric acid and 5 ml of acetic acid. The resultant solution was heated under reflux for 1 hour. The reaction mixture was concentrated to dryness under reduced pressure. The residue thus obtained was recrystallized from ethanol, whereby 120 mg of the title compound was obtained as colorless needle crystals.

Melting point: 212°–215° C.
¹H-NMR (DMSO-d₆) δ: 1.05–1.25(m,4H), 2.00–2.27(m,2H), 3.54(brs,2H), 3.98(s,3H), 4.20(m,1H), 5.22(brs,1H), 7.94(d,1H,J=11Hz), 8.73(s,1H).

EXAMPLE 21

7-(1-Formimidoyl-3-pyrrolidinyloxy)-1-cyclopropyl-5-amino-6,8-difluoro-1,4-dihydro-4-oxoquinoline-3-carboxylic acid hydrochloride (Compound No. 44)

To a mixture of 100 mg of 7-(3-pyrrolidinyloxy)-1-cyclopropyl-5-amino-6,8-difluoro-1,4-dihydro-4-oxoquinoline-3-carboxylic acid hydrochloride (Compound No. 8), 152 mg of DBU and 8 ml of ethanol was added 71 mg of benzyl formimidate while the former was stirred at room temperature. The resultant mixture was stirred for 6 hours, to which 2 ml of HCl-saturated ethanol was added. Crystals thus precipitated were collected by filtration. They were successively washed with ethanol and ether, whereby 39 mg of the title compound was obtained as pale green needle crystals.

Melting point: 240°–242° C. (decomposed).
¹H-NMR (DMSO-d₆) δ: 1.00–1.25(m,4H), 2.04–2.50(m,2H), 4.05(m,1H), 5.25(brs,1H), 7.50(brs,2H), 8.27(m,1H), 8.57(s,1H).

EXAMPLE 22

Compound Nos. 45–46 shown in Table 7 were obtained in a similar manner to Example 21.

TABLE 7

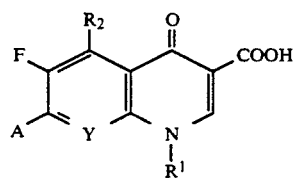

| Comp'd. No. | R¹ | R² | A | Y | Melting point (°C.) | Form | (Solvent) ¹H-NMR(δ) |
|---|---|---|---|---|---|---|---|
| 45 | cyclopropyl | H | piperidinyl-CH₂O— (HCl) (2'R) form | CF | 177–181 | Colorless powder (optically active) | (DMSO-d₆-D₂O): 1.05–1.30(m, 4H), 1.95–2.20(m, 4H), 4.14(m, 1H), 4.48(brs, 2H), 8.00(d, 1H, J=7Hz), 8.27(m, 1H), 8.74(s, 1H) |
| 56 | cyclopropyl | NH₂ | piperidinyl-O (HCl) HN=C-CH₃ | CF | 248–255 (decomposed) | Pale yellow powder | (DMSO-d₆): 1.05–1.25(m, 4H), 2.31(s, 3H), 2.35(s, 2H), 3.76(m, 1H), 3.96(m, 1H), 4.02(m, 1H), 5.28(brs, 1H), 7.53(brs, 2H), 8.56(s, 1H) |

EXAMPLE 23

7-[N-methyl-(1-methyl-3-pyrrolidinylmethyl)]amino-1-cyclopropyl-6-fluoro-1,4-dihydro-4-oxoquinoline-3-carboxylic acid (Compound No. 47)

A mixture of 265 mg of 1-cyclopropyl-6,7-difluoro-1,4-dihydro-4-oxoquinoline-3-carboxylic acid, 384 mg of 1-methyl-3-(methylamino)methylpyrrolidine and 2 ml of DMF was stirred at 100° C. for 1 hour. The reaction mixture was allowed to cool down, followed by dilution with chloroform. The resultant chloroform solution was washed with water and then dried over anhydrous magnesium sulfate. The solvent was distilled off. The residue was recrystallized from ethyl acetate, so that 260 mg of the title compound was obtained.

Melting point: 220°–223° C. (decomposed).
¹H-NMR (DMSO-d₆) δ: 0.96–1.27(m,4H), 1.43(m,1H), 1.88(m,1H), 2.22(s,3H), 2.47(m,4H), 3.00(s,3H), 3.32(m,3H), 4.02(m,1H), 7.32–7.78(m,2H), 8.58(s,1H).

EXAMPLE 24

Compound Nos 48–51 shown in Table 8 were obtained in a similar manner to Example 23.

TABLE 8

Structure:
F–(ring)–R2, with 6-position C=O, 3-COOH, N-R1, 7-position A, 8-position Y

| Comp'd. No. | R¹ | R² | A | Y | Melting point (°C.) | Form | (Solvent) ¹H-NMR(δ) |
|---|---|---|---|---|---|---|---|
| 48 | cyclopropyl | NH₂ | 4-(N-methyl-3-(N-methylaminomethyl)piperidinyl) | | CF 168–171 | | (DMSO-d₆): 1.08(m, 4H), 1.35(m, 1H), 1.84(m, 1H), 2,18(s, 3H), 2.30–2.51(m, 4H), 3.00(s, 3H), 3.22–3.38(m, 3H), 4.04(m, 1H), 7.23(brs, 2H), 8.50(s, 1H) |
| 49 | cyclopropyl | H | 4-(N-methyl-3-(N-methylaminomethyl)piperidinyl) | | CF 175–179 (decomposed) | | (DMSO-d₆): 0.98–1.10(m, 4H), 1.33(m, 1H), 1.84(m, 1H), 2.18(s, 3H), 2.32–2.54(m, 4H), 2.93(s, 3H), 3.18(m, 3H), 4.02(m, 1H), 7.45(m, 1H), 8.65(s, 1H) |
| 50 | cyclopropyl | H | (Et-N)(Et-N)CH piperazinyl-N–H | | CH 240–243 (decomposed) | Colorless powder | (CDCl₃): 1.12(t, 3H, J=7Hz), 1.15–1.25(m, 2H), 1.31–1.40 (m, 2H), 2.74(q, 2H, J=7Hz), 2.95(dd, 2H, J=11Hz, 4Hz), 3.41(dd, 2H, J=11Hz, 6Hz), 3.49–3.58(m, 1H), 4.29–4.40(m, 1H), 5.00(brs, 1H), 7.02(d, 1H, J=7Hz), 7.94(d, 1H, J=11Hz), 8.70(s, 1H) |
| 51 | cyclopropyl | H | (Et-N)(Et-N)CH piperazinyl-N–H | | CF 187–191 | Colorless powder | (CDCl₃): 1.11(t, 3H, J=7Hz), 1.12–1.32(m, 4H), 2.72(q, 2H, J=7Hz), 2.89(dd, 2H, J=11Hz, 4Hz), 3.29(dd, 2H, J=11Hz, 6Hz), 3.92–4.02(m, 1H), 4.50–4.60(m, 1H), 4.69(brs, 1H), 7.90(dd, 1H, J=12Hz, 2Hz), 8.74(s, 1H) |

EXAMPLE 25

7-(4-Piperidyloxy)-1-cyclopropyl-5-amino-8-fluoro-1,4-dihydro-4-oxoquinoline-3-carboxylic acid (Compound No. 52)

1-Cyclopropyl-5-amino-7,8-difluoro-1,4-dihydro-4-oxoquinoline-3-carboxylic acid, 4-piperidinol and sodium hydride were reacted and treated in a similar manner to Example 9, whereby the title compound was obtained as colorless powder.

Melting point: >300° C.
¹H-NMR (DMSO-d₆) δ: 1.06–1.30(m,4H), 1.54–1.67(m,2H), 1.88–2.00(m,2H), 2.44–2.57(m,2H), 2.93–3.05(m,2H), 3.94–4.04(m,1H), 4.35–4.47(m,1H), 6.82(d,1H,J=6Hz), 7.43(brs,2H), 8.68(s,1H).

EXAMPLE 26

Ethyl 1-cyclopropyl-6-fluoro-7-(3-oxazolidinyl)-1,4-dihydro-4-oxoquinoline-3-carboxylate (Compound No. 53)

1) A mixture of 2.94 g of ethyl 1-cyclopropyl-6,7-difluoro-1,4-dihydro-4-oxoquinoline-3-carboxylate, 1.83 g of monoethanolamine and 20 ml of dimethylformamide was heated at 90°–100° C. for 1 hour under stirring. The reaction mixture was concentrated to dryness under reduced pressure. To the residue was added 100 ml of chloroform, so that the residue was dissolved. The chloroform solution thus obtained was washed successively with 5% acetic acid and saturated saline, dried over anhydrous magnesium sulfate and then concentrated.

The residue was recrystallized from a mixed solvent of diethyl ether and ethanol, whereby 3.0 g of ethyl 1-cyclopropyl-6-fluoro-7-(2-hydroxyethylamino)-1,4-dihydro-4-oxoquinoline-3-carboxylate was obtained.

Melting point: 228°–230° C.

2) A mixture of 0.67 g of ethyl 1-cyclopropyl-6-fluoro-7-(2-hydroxyethylamino)-1,4-dihydro-4-oxoquinoline-3-carboxylate, 0.08 g of p-toluenesulfonic acid, 2.08 g of diethoxymethane and 20 ml of acetonitrile was stirred for 3 hours under reflux. After the reaction mixture was allowed to cool down, 100 ml of chloroform was added to the reaction mixture. The resultant mixture was successively washed with 5% aq. sodium carbonate solution and saturated saline, dried over anhydrous magnesium sulfate and then concentrated.

The residue was purified by columnchromatography on silica gel, whereby 0.39 g of the title compound was obtained.

Melting point: 221°–224° C.
¹H-NMR (CDCl₃) δ: 1.12–1.30(m,4H), 1.40(t,3H,J=7.1Hz), 3.39(m,1H), 3.60(t,2H,J=6.0Hz), 4.19(q,2H,J=7.1Hz), 4.19(t,2H,J=6.0Hz), 4.38(d,2H,J=7.1Hz), 6.82(d,1H,J=7.1Hz), 7.98(d,1H,J=13.7Hz), 8.45(s,1H)

EXAMPLE 27

Compound Nos. 54–56 shown in Table 9 were synthesized in a similar manner to Example 26.

The reaction mixture was allowed to cool down and then acidified with acetic acid. Crystals thus precipitated were collected by filtration, washed with water and ethanol, and then dried, whereby 140 mg of the title compound was obtained.

Melting point: 293°–295° C. (decomposed).

$^1$H-NMR (DMSO-d$_6$) δ: 1.12–1.31(m,4H), 3.68(m,3H), 4.17(m,2H), 5.12(m,2H), 7.12(d,1H,J=6.0Hz), 7.87(d,1H,J=13.2Hz), 8.60(s,1H).

TABLE 9

| Comp'd. No. | R$^1$ | R$^3$ | A | Y | Melting point (°C.) | (Solvent) $^1$H-NMR |
|---|---|---|---|---|---|---|
| 54 | —C$_2$H$_5$ | H | (oxazolidinyl) | CH | 169–172 | (CDCl$_3$): 8.33(s, 1H), 8.02(d, 1H, J=13.7Hz), 6.27(d, 1H, J=6.6Hz), 5.08(d, 2H, J=3.3Hz), 4.38(q, 2H, J=7.1Hz), 4.18(m, 4H), 3.56(m, 2H), 1.51(t, 3H, J=7.1Hz), 1.40(t, 3H, J=7.1Hz) |
| 55 | cyclopropyl | H | Me-(oxazolidinyl) | CH | 181–184 | (CDCl$_3$): 8.46(s, 1H), 8.00(d, 1H, J=14.3Hz), 6.77(d, 1H, J=7.1Hz), 5.20(m, 1H), 5.09(m, 1H), 4.38(m, 3H), 3.67(m, 1H), 3.38(m, 1H), 3.17(m, 1H) 1.43(d, 3H, J=6.0Hz), 1.40(t, 3H, J=7.1Hz), 1.12–1.31(m, 4H) |
| 56 | cyclopropyl | H | Me,Me-N-(oxazolidinyl) | CH | 169–172 | (CDCl$_3$): 8.46(s, 1H), 7.99(d, 1H, J=13.7Hz), 6.80(d, 1H, J=7.1Hz), 5.22(m, 1H), 5.10(m, 1H), 4.37(m, 3H), 3.66(m, 1H), 3.35(m, 2H), 2.65(m, 2H), 2.38(s, 6H), 1.40(t, 3H, J=7.1Hz, 1.12–1.43(m, 4H) |

EXAMPLE 8

1-Cyclopropyl-6-fluoro-7-(3-oxazolidinyl)-1,4-dihydro-4-oxoquinoline-3-carboxylic acid (Compound No. 57)

A mixture of 173 mg of ethyl 1-cyclopropyl-6-fluoro-7-(3-oxazolidinyl)-1,4-dihydro-4-oxoquinoline-3-carboxylate, 1 ml of ethanol and 5 ml of a 10% aq. sodium carbonate solution was stirred for 1 hour under reflux.

EXAMPLE 29

Compound Nos. 58–60 shown in Table 10 were synthesized in a similar manner to Example 28.

TABLE 10

| Comp'd. No. | R$^1$ | R$^3$ | A | Y | Melting point (°C.) | (Solvent) $^1$H-NMR |
|---|---|---|---|---|---|---|
| 58 | —C$_2$H$_5$ | H | (oxazolidinyl) | CH | 292–295 (decomposed) | (DMSO-d$_6$): 8.89(s, 1H), 7.89(d, 1H, J=14.3Hz), 6.76(d, 1H, J=7.2Hz), 5.10(d, 2H, J=2.8Hz), 4.55(q, 2H, J=6.6Hz), 4.14(m, 2H), 3.67(m, 2H), 1.41(t, 3H, J=6.6Hz) |
| 59 | cyclopropyl | H | Me-(oxazolidinyl) | CH | 276–279 | (DMSO-d$_6$): 8.60(s, 1H), 7.86(d, 1H, J=13.2Hz), 7.08(d, 1H, J=6.0Hz), 5.25(m, 1H), 5.06(m, 1H), 4.35(m, 1H), 3.77(m, 2H), 1.38(d, 3H, J=6.0Hz), 1.15(m, 4H) |

TABLE 10-continued

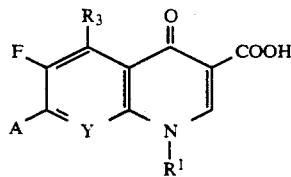

| Comp'd. No. | R¹ | R³ | A | Y | Melting point (°C.) | (Solvent) ¹H-NMR |
|---|---|---|---|---|---|---|
| 60 | ▷ | H | Me₂N-CH(CH₂-)CH₂- (with oxazolidinyl) | CH | 232–235 (decomposed) | (DMSO-$d_6$): 8.60(s, 1H), 7.89(d, 1H, J=13.2Hz), 7.10(d, 1H, J=6.0Hz), 5.25(m, 1H), 5.08(m, 1H), 4.42(m, 1H), 3.78 (m, 2H), 2.59(m, 2H), 2.26(s, 6H), 1.16–1.31(m, 4H) |

EXAMPLE 30

Ethyl 1-cyclopropyl-6,8-difluoro-7-(3-oxazolidinyl)-1,4-dihydro-4-oxoquinoline-3-carboxylate (Compound No. 61)

1) A mixture of 9.33 g of ethyl 1-cyclopropyl-6,7,8-trifluoro-1,4-dihydro-4-oxoquinoline-3-carboxylate, 5.49 g of monoethanolamine and 50 ml of dimethylformamide was heated at 90°–100° C. for 1 hour under stirring. The reaction mixture was concentrated to dryness under reduced pressure. To the residue thus obtained was added 150 ml of chloroorm, so that the residue was dissolved. The chloroform solution was successively washed with 5% acetic acid and saturated saline, dried over anhydrous magnesium sulfate, and then concentrated.

The residue was recrystallized from a mixed solvent of diethyl ether and ethanol, whereby 6.42 g of ethyl 1-cyclopropyl-6,8-difluoro-7-(2-hydroxyethylamino)-1,4-dihydro-4-oxoquinoline-3-carboxylate was obtained.

Melting point: 171°–173° C.

2) A mixture of 0.70 g of ethyl 1-cyclopropyl-6,8-difluoro-7-(2-hydroxyethylamino)-1,4-dihydro-4-oxoquinoline-3-carboxylate, 0.08 g of p-toluenesulfonic acid, 2.08 g of diethoxymethane and 20 ml of acetonitrile was stirred for 3 hours under reflux. The reaction mixture was allowed to cool down, followed by the addition of 100 ml of chloroform. The resultant mixture was washed successively with 5% aq. sodium carbonate solution and saturated saline, dried over anhydrous magnesium sulfate, and then concentrated.

The residue was purified by columnchromatography on silica gel, whereby 0.30 g of the title compound was obtained.

Melting point: 178°–181° C.

¹H-NMR (CDCl₃) δ: 1.10–1.23(m,4H), 1.40(t,3H), 3.82(m,3H), 4.09(t,2H,J=6.0Hz), 4.38(q,2H,J=7.1Hz), 5.09(s,2H), 7.89(d,1H,J=13.7Hz), 8.50(s,1H).

EXAMPLE 31

Compound Nos. 62–65 shown in Table 11 were synthesized in a similar manner to Example 30.

TABLE 11

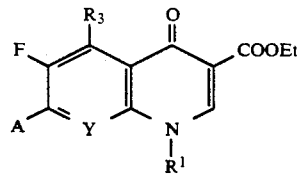

| Comp'd. No. | R¹ | R³ | A | Y | Melting point (°C.) | (Solvent) ¹H-NMR |
|---|---|---|---|---|---|---|
| 62 | ▷ | H | Me-CH(-)CH₂-N(-O-) | CF | 141–144 | (CDCl₃): 8.49(s, 1H), 7.86(dd, 1H, J=1.7Hz, 13.7Hz), 5.15 (m, 2H), 4.37(q, 2H, J=7.1Hz), 4.21(m, 1H), 3.83(m, 2H), 3.46(m, 1H), 1.43(d, 3H, J=6.0Hz), 1.42(t, 3H, J=7.1Hz), 1.10–1.22(m, 4H) |
| 63 | ▷ | H | -CH₂-CH(Me)-N(-O-) | CF | 150–152 | (CDCl₃): 8.51(s, 1H), 7.90(dd, 1H, J=13.7Hz, 1.6Hz), 5.19 (m, 1H), 4.92(m, 1H), 4.38(m, 4H), 3.86(m, 1H), 3.57(m, 1H), 1.40(t, 3H, J=7.1Hz), 1.23(d, 3H, J=6.1Hz), 1.10–1.30(m, 4H) |

TABLE 11-continued

| Comp'd. No. | R¹ | R³ | A | Y | Melting point (°C.) | (Solvent) ¹H-NMR |
|---|---|---|---|---|---|---|
| 64 | cyclopropyl | H | Me₂N-CH(CH₂-)- (morpholine-like) | | CF | 131-133 | (CDCl₃): 8.50(s, 1H), 7.88(dd, 1H, J=1.7Hz, 13.7Hz), 5.16(m, 2H), 4.34(m, 3H), 3.81(m, 2H), 3.55(m, 1H), 2.60(m, 2H), 2.35(s, 6H), 1.40(t, 3H, J=7.1Hz), 1.09-1.21(m, 4H) |
| 65 | cyclopropyl | H | MeO-CH(CH₂-)- | CF | 131 | (CDCl₃): 8.49(s, 1H), 7.85(dd, 1H, J=2.2Hz, 13.7Hz), 5.15 (m, 2H), 4.36(q, 2H, J=7.1Hz), 4.29(m, 1H), 3.81 (m, 2H), 3.69(m, 1H), 3.62(d, 2H, J=5.0Hz), 3.44 (s, 3H), 1.38(t, 3H, J=7.1Hz), 1.08-1.22(m, 4H) |

EXAMPLE 32

1-Cyclopropyl-6,8-difluoro-7-(3-oxazolidinyl)-1,4-dihydro-4-oxoquinoline-3-carboxylic acid (Compound No. 66)

A mixture of 182 mg of ethyl 1-cyclopropyl-6,8-difluoro-7-(3-oxazolidinyl)-1,4-dihydro-4-oxoquinoline-3-carboxylate, 5 ml of ethanol and 10 ml of 10% aq. sodium carbonate solution was stirred for 1 hour under reflux. The reaction mixture was allowed to cool down and then acidified with acetic acid. Crystals thus precipitated were collected by filtration. They were washed with water and ethanol and then dried, whereby 112 mg of the title compound was obtained.

Melting point: 261°-264° C. (decomposed).

¹H-NMR (DMSO-d₆) δ: 1.18(m,4H), 3.80(m,2H), 4.05(m,3H), 5.10(m,2H), 7.76(d,1H,J=13.7Hz), 8.62(s,1H).

EXAMPLE 33

Compound Nos. 67-70 shown in Table 12 were synthesized in a similar manner to Example 32.

TABLE 12

| Comp'd. No. | R¹ | R³ | A | Y | Melting point (°C.) | (Solvent) ¹H-NMR |
|---|---|---|---|---|---|---|
| 67 | cyclopropyl | H | Me-CH(CH₂-)- | CF | 241-244 | (DMSO-d₆): 8.72(s, 1H), 7.85(dd, 1H, J=1.7Hz, 13.7Hz), 5.21(m, 2H), 4.21(m, 1H), 3.86-4.00(m, 2H) 3.52(m, 1H), 1.45(d, 3H, J=6.1Hz), 1.15-1.30(m, 4H) |
| 68 | cyclopropyl | H | Me-CH(CH₂-)- | CF | 186-189 | (DMSO-d₆): 8.73(s, 1H), 7.86(dd, 1H, J=1.7Hz, 13.2Hz), 5.25(m, 1H), 5.00(m, 1H), 4.48(m, 1H), 4.36(m, 1H), 4.00(m, 1H), 3.60(m, 1H), 1.27(d, 3H, J=6.0Hz), 1.12-1.36(m, 4H) |
| 69 | cyclopropyl | H | Me₂N-CH(CH₂-)- | CF | 192-195 (decomposed) | (DMSO-d₆): 8.64(s, 1H), 7.75(d, 1H, J=13.7Hz), 5.20(m, 1H), 5.12(m, 1H), 4.28(m, 1H), 4.07(m, 1H), 3.85(m, 1H), 3.53(m, 1H), 2.58(m, 2H), 2.24(s, 6H), 1.19(m, 4H) |

TABLE 12-continued

| Comp'd. No. | R¹ | R³ | A | Y | Melting point (°C.) | (Solvent) ¹H-NMR |
|---|---|---|---|---|---|---|
| 70 | ◁ | H | 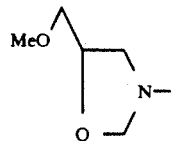 | CF | 172–173 | (DMSO-d$_6$): 8.58(s, 1H), 7.67(d, 1H, J=13.7Hz), 5.21(m, 1H), 5.12(m, 1H), 4.30(m, 1H), 4.06(m, 1H), 3.85(m, 1H), 3.58(m, 3H), 3.33(s, 3H), 1.19(m, 4H) |

EXAMPLE 34

Ethyl 1-cyclopropyl-5,6,8-trifluoro-7-(3-oxazolidinyl)-1,4-dihydro-4-oxoquinoline-3-carboxylate (Compound No. 71)

1) A mixture of 9.87 g of ethyl 1-cyclopropyl-5,6,7,8-tetrafluoro-1,4-dihydro-4-oxoquinoline-3-carboxylate, 5.49 g of monoethanolamine and 60 ml of dimethylformamide was heated at 90°–100° C. for 1 hour under stirring. The reaction mixture was concentrated to dryness under reduced pressure. To the residue thus obtained was added 300 ml of chloroform so that the residue was dissolved. The chloroform solution was washed successively with 5% acetic acid and saturated saline, dried over anhydrous magnesium sulfate, and then concentrated.

The residue was purified by columnchromatography on silica gel, whereby 3.20 g of ethyl 1-cyclopropyl-5,6,8-trifluoro-7-(2-hydroxyethylamino)-1,4-dihydro-4-oxoquinoline-3-carboxylate was obtained.

Melting point: 193°–195° C.

2) A mixture of 0.74 g of ethyl 1-cyclopropyl-5,6,8-trifluoro-7-(2-hydroxyethylamino)-1,4-dihydro-4-oxoquinoline-3-carboxylate, 0.08 g of p-toluenesulfonic acid, 2.08 g of diethoxymethane and 20 ml of acetonitrile was stirred for 3 hours under reflux. The reaction mixture was allowed to cool down, followed by the addition of 100 ml of chloroform. The resultant mixture was washed successively with 5% aq. sodium carbonate solution and saturated saline, dried over anhydrous magnesium sulfate, and then concentrated.

The residue was purified by columnchromatography on silica gel, whereby 0.32 g of the title compound was obtained.

Melting point: 182°–185° C.

¹H-NMR (CDCl$_3$) δ: 1.06–1.22(m,4H), 1.38(t,3H,J=7.1Hz), 3.83(m,3H) 4.11(t,2H,J=6.0Hz), 4.35(q,2H,J=7.1Hz), 5.11(t,2H,J=2.8Hz), 8.39(s,1H).

EXAMPLE 35

1-Cyclopropyl-5,6,8-trifluoro-7-(3-oxazolidinyl)-1,4-dihydro-4-oxoquinoline-3-carboxylic acid (Compound No. 72)

A mixture of 191 mg of ethyl 1-cyclopropyl-5,6,8-trifluoro-7-(3-oxazolidinyl)-1,4-dihydro-4-oxoquinoline-3-carboxylate, 1 ml of ethanol and 5 ml of 10% aq. sodium carbonate solution was stirred for 1 hour under reflux. The reaction mixture was allowed to cool down and then acidified with acetic acid. Crystals thus precipitated were collected by filtration. They were washed with water and ethanol and then dried, whereby 163 mg of the title compound was obtained.

Melting point: 290°–293° C. (decomposed).

¹H-NMR (DMSO-d$_6$) δ: 1.13(m,4H), 3.83(m,1H), 4.70(m,2H), 5.13(m,2H), 8.60(s,1H).

EXAMPLE 36

Ethyl 1-cyclopropyl-6,8-difluoro-7-(5-benzoyloxymethyl-3-oxazolidinyl)-1,4-dihydro-4-oxoquinoline-3-carboxylate (Compound No. 73)

1) A mixture of 6.22 g of ethyl 1-cyclopropyl-6,7,8-trifluoro-1,4-dihydro-4-oxoquinoline-3-carboxylate, 5.46 g of 3-aminopropane-1,2-diol and 40 ml of dimethylformamide was heated at 90–100° C. for 1 hour under stirring. The reaction mixture was concentrated to dryness under reduced pressure. To the residue was added 200 ml of chloroform, so that the residue was dissolved. The resultant chloroform solution was washed successively with 5% acetic acid and saturated saline, dried over anhydrous magnesium sulfate, and then concentrated.

The residue thus obtained was recrystallized from diethyl ether, whereby 5.40 g of ethyl 1-cyclopropyl-6,8-difluoro-7-(2,3-dihydroxypropylamino)-1,4-dihydro-4-oxoquinoline-3-carboxylate was obtained.

Melting point: 173°–175° C.

2) A mixture of 3.82 g of ethyl 1-cyclopropyl-6,8-difluoro-7-(2,3-dihydroxypropylamino)-1,4-dihydro-4-oxoquinoline-3-carboxylate, 2.30 g of benzoic anhydride, 0.12 g of 4-dimethylaminopyridine and 50 ml of dimethylformamide was reacted for 1 hour at room temperature. The reaction mixture was concentrated under reduced pressure and the residue was dissolved in 150 ml of chloroform. The resultant chloroform solution was washed successively with 5% acetic acid, water, saturated aq. sodium hydrogencarbonate solution and saturated saline, dried over anhydrous magnesium sulfate, and then evaporated.

The residue thus obtained was purified by columnchromatography on silica gel, whereby 1.35 g of ethyl 1-cyclopropyl-6,8-difluoro-7-(3-benzoyloxy-2-hydroxypropylamino)-1,4-dihydro-4-oxoquinoline-3-carboxylate was obtained.

Melting point: 134°–136° C.

3) A mixture of 1.22 g of ethyl 1-cyclopropyl-6,8-difluoro-7-(3-benzoyloxy-2-hydroxypropylamino)-1,4-dihydro-4-oxoquinoline-3-carboxylate, 2.6 g of diethoxymethane, 100 mg of p-toluenesulfonic acid hydrate and 25 ml of acetonitrile was stirred for 4 hours under reflux. After the reaction mixture was allowed to cool down, 100 ml of chloroform was added to the reaction mixture. The resultant mixture was washed successively with 5% aq. sodium carbonate solution and saturated saline, dried over anhydrous magnesium sulfate, and then evaporated.

The residue thus obtained was purified by column-chromatography on silica gel, whereby 0.57 g of the title compound was obtained.

Melting point: 120°-123° C.
$^1$H-HMR (CDCl$_3$) δ: 1.08–1.21(m,4H), 1.40(t,3H,J=7.1Hz , 3.75–3.96(m,3H), 4.38(q,2H,J=7.1Hz), 4.55(m,3H), 5.14(m,1H), 5.24(m,1H), 7.90(dd,1H,J=1.7Hz,13.7Hz), 7.40–8.05(m,5H), 8.50(s,1H).

EXAMPLE 37

1-Cyclopropyl-6,8-difluoro-7-(5-hydroxymethyl-3-oxazolidinyl)-1,4-dihydro-4-oxoquinoline-3-carboxylic acid (Compound No. 74)

A mixture of 250 mg of ethyl 1-cyclopropyl-6,8-difluoro-7-(5-benzoyloxymethyl-3-oxazolidinyl)-1,4-dihydro-4-oxoquinoline-3-carboxylate, 2 ml of ethanol and 10 ml of 10% aq. sodium carbonate solution was stirred under reflux for 1 hour. The reaction mixture was allowed to cool down and then acidified with acetic acid. Crystals thus precipitated were collected by filtration. They were washed with water and ethanol and then dried, whereby 162 mg of the title compound was obtained.

Melting point: 209°-212° C. (decomposed).
$^1$H-NMR (DMSO-d$_6$) δ: 1.17(m,4H), 3.62(m,2H), 3.81(m,1H), 4.06(m,1H), 4.16(m,1H), 4.96(m,1H), 5.11(m,1H), 5.21(m,1H), 7.71(d,1H,J=13.6Hz), 8.60(s,1H).

EXAMPLE 38

Ethyl 1-cyclopropyl-6,8-difluoro-7-(tetrahydro-1,3-oxazin)-3-yl-1,4-dihydro-4-oxoquinoline-3-carboxylate (Compound No. 75)

1) A mixture of 1.71 g of ethyl 1-cyclopropyl-6,7,8-trifluoro-1,4-dihydro-4-oxoquinoline-3-carboxylate, 1.13 g of 3-aminopropanol and 10 ml of dimethylformamide was heated at 90°-100° C. for 1 hour under stirring. The reaction mixture was concentrated to dryness under reduced pressure. To the residue was added 50 ml of chloroform, so that the residue was dissolved. The resultant chloroform solution was washed successively with 5% acetic acid and saturated saline, dried over anhydrous magnesium sulfate, and then concentrated.

The residue thus obtained was recrystallized from diethyl ether, whereby 1.54 g of ethyl 1-cyclopropyl-6,8-difluoro-7-(3-hydroxypropylamino)-1,4-dihydro-4-oxoquinoline-3-carboxylate was obtained.

Melting point: 160°-162° C.

2) A mixture of 0.37 g of ethyl 1-cyclopropyl-6,8-difluoro-7-(3-hydroxypropylamino)-1,4-dihydro-4-oxoquinoline-3-carboxylate, 0.04 g of p-toluenesulfonic acid, 1.04 g of diethoxymethane and 10 ml of acetonitrile was stirred for 3 hours under reflux. After the reaction mixture was allowed to cool down, 50 ml of chloroform was added to the reaction mixture. The resultant mixture was washed successively with 5% aq. sodium carbonate solution and saturated saline, dried over anhydrous magnesium sulfate, and then evaporated.

The residue thus obtained was purified by column-chromatography on silica gel, whereby 0.20 g of the title compound was obtained.

Melting point: 171°-173° C.
$^1$H-NMR (CDCl$_3$) δ: 1.11–1.25(m,4H), 1.40(t,3H,J=7.1Hz , 1.89 (m,2H), 3.59(m,2H), 3.88(m,1H), 3.98(m,2H), 4.38(q,2H,J=7.1Hz), 4.85(s,2H), 7.91(dd,1H,J=1.7Hz,12.1Hz), 8.53(s,1H).

EXAMPLE 39

Cyclopropyl-6,8-difluoro-7-(tetrahydro-1,3-oxazin)-3-yl-1,4-dihydro-4-oxoquinoline-3-carboxylic acid (Compound No. 76)

A mixture of 170 mg of ethyl 1-cyclopropyl-6,8-difluoro-7-(tetrahydro-1,3-oxazin)-3-yl-1,4-dihydro-4-oxoquinoline-3-carboxylate, 1 ml of ethanol and 5 ml of 10% aq. sodium carbonate solution was stirred for 1 hour under reflux. The reaction mixture was allowed to cool down, followed by the addition of acetic acid to acidify the same. Crystals thus precipitated were collected by filtration, washed with water and ethanol, and then dried, whereby 81 mg of the title compound was obtained.

Melting point: 215°-218° C.
$^1$H-NMR (DMSO-d$_6$) δ: 1.20(m,4H), 1.78(m,2H), 3.61*m,2H), 3.91(m,2H), 4.13(m,1H), 4.84(s,2H), 7.83(d,1H,J=11.5Hz), 8.68(s,1H).

EXAMPLE 40

7-(1-Morpholinooxy)-1-cyclopropyl-6-fluoro-1,4-dihydro-4-oxoquinoline-3-carboxylic acid (Compound No. 77)

In a manner similar to Example 9, the title compound was obtained using 1-cyclopropyl-6,7-difluoro-1,4-dihydro-4-oxoquinolin-3-carboxylic acid, 1-hydroxymorpholine and sodium hydride.

Melting point: 170°-174° C. (decomposed).
$^1$H-NMR (DMSO-d6) δ: 1.22–1.34(m,4H), 3.00(m,2H), 3.41(m,2H), 3.71(m,2H), 3.87(m,1H), 4.02(m,2H), 8.03(d,1H,J=9Hz), 8.26(d,1H,J=12Hz), 8.72(s,1H).

We claim:

1. A compound of the formula I or a pharmaceutically acceptable salt thereof:

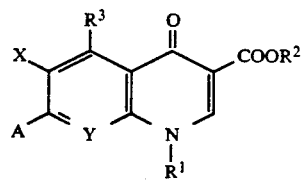

wherein R$^1$ is lower alkyl, halo-lower alkyl, hydroxy-lower alkyl, C$_3$–C$_7$-cycloalkyl, lower alkyl-C$_3$–C$_7$-cycloalkyl, lower alkenyl, phenyl or substituted phenyl, wherein the substituents are independently selected from the group consisting of halo, lower alkoxy, acetyloxy, hydroxy, amino, lower alkyl and nitro; R$^2$ denotes a hydrogen atom, lower alkyl, aralkyl, aryl, lower alkanyloxy-lower alkyl, lower alkoxy-carbonyloxy-lower alkyl, lower alkoxymethyl, di(lower alkyl)amino-lower alkyl; (5-methyl-2-oxol-4-yl)methyl, or phthalidyl; R$^3$ represents hydrogen, halo, amino, mono- or di-(lower alkyl)amino, hydroxy or lower alkoxy; X is hydrogen or halo; Y is C—R⁴ in which R⁴ is hydrogen, halo, lower alkyl or lower alkoxy, A denotes a substituted or unsubstituted 3-oxazolidinyl group or a substituted or unsubstituted tetrahydro-1,3-oxazin-3-yl group wherein said substituents are independently selected from the group consisting of lower alkyl, hydroxy-lower alkyl, lower alkoxy-lower alkyl, amino-lower alkyl, mono- or di-(lower alkyl)amino-lower alkyl, hydroxy, lower alkoxy, amino, and mono- or di(lower alkyl)amino; —Z—(CH₂)ₙ—B is which Z is an oxygen atom or a group H—R⁵, wherein R⁵ is hydrogen, lower alkyl or benzyl, B is selected from the group consisting of

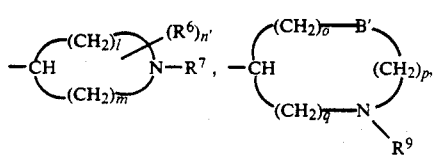

and

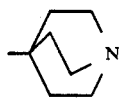

wherein B' means an oxygen or sulfur atom or N—R⁸, n' groups of R⁶ may be the same or different and individually mean a hydrogen atom or a lower alkyl group; R⁷ is a member selected from the group consisting of formidoyl, acetimidoyl and benzimidoyl; R⁸ and R⁹ are the same or different and are selected from the group consisting of hydrogen, lower alkyl, halo-lower alkyl, hydroxy-lower alkyl, methoxy-lower alkyl, amino-lower alkyl, lower alkoxycarbonyl; carboxy-lower alkyl; C₃–C₅-cycloalkyl, benzyl, acetyl, benzoyl, trifluoroacetyl, lower alkoxycarbonyl and benzyloxycarbonyl and l stands for an integer of 1–3, m is 1, n' an integer of 1–4, o an integer of 0 or 1, p an integer of 0–2, and q an integer of 0 or 1, the sum of o+p+q being 2; and n stands for an integer of 0–2, provided that R¹ is not ethyl when R⁶ is hydrogen.

2. An antibacterial composition comprising a carrier and, as an active ingredient, an antibacterially effective amount of the quinolone derivative or a pharmaceutically acceptable salt thereof according to claim 1.

3. A quinoline derivative according to claim 1, 1-cyclopropyl-6,8-difluoro-7-(5-hydroxymethyl-3-oxazolidinyl)-1,4-dihydro-4-oxoquinoline-3-carboxylic acid or a pharmaceutically acceptable salt thereof.

4. An antibacterial composition comprising a carrier and, as an active ingredient, an antibacterially effective amount of the quinoline derivative or a pharmaceutically acceptable salt thereof according to claim 3.

5. A compound of the formula I or a pharmaceutically acceptable salt thereof:

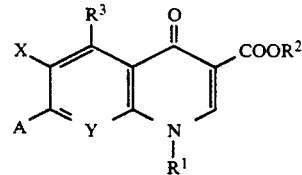

wherein R¹ is lower alkyl, halo-lower alkyl, hydroxy-lower alkyl, C₃–C₇-cycloalkyl, lower alkyl-C₃–C₇-cycloalkyl, lower alkenyl, phenyl or substituted phenyl, wherein the substituents are independently selected from the group consisting of halo, lower alkoxy, acetyloxy, hydroxy, amino, lower alkyl and nitro; R² denotes a hydrogen atom, lower alkyl, aralkyl, aryl, lower alkanoyloxy-lower alkyl, lower alkoxy-carbonyloxy-lower alkyl, lower alkoxymethyl, di(lower alkyl)amino-lower alkyl; (5-methyl-2-oxol-4-yl)methyl, or phthalidyl; R³ represents hydrogen, halo, amino, mono- or di(lower alkyl)amino, hydroxyl or lower alkoxy; X is hydrogen or halo; Y is C—R⁴ in which R⁴ is hydrogen, halo, lower alkyl or lower alkoxy, A denotes a substituted or unsubstituted 3-oxazolidinyl group or a substituted or unsubstituted tetrahydro-1,3-oxazin-3-yl group wherein said substituents are independently selected from the group consisting of lower alkyl, hydroxy-lower alkyl, lower alkoxy-lower alkyl, amino-lower alkyl, mono- or di-(lower alkyl)amino-lower alkyl, hydroxyl, lower alkoxy, amino, and mono- or di(lower alkyl)amino; —Z—(CH₂)ₙ—B in which Z is an oxygen atom or a group N—R⁵, wherein R⁵ is hydrogen, lower alkyl or benzyl, B is selected from the group consisting of

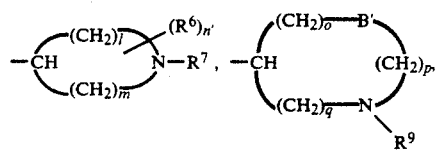

and

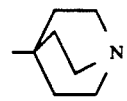

wherein B' means an oxygen or sulfur atom or N—R⁸, n' groups of R⁶ may be the same or different and individually mean a hydrogen atom or a lower alkyl group; R⁷ is a member selected from the group consisting of halo-lower alkyl, hydroxy-lower alkyl, methoxy-lower alkyl, amino-lower alkyl, cyano-lower alkyl, ethoxycarbonyl-lower alkyl, carboxy-lower alkyl, formidoyl, acetimidoyl and benzimidoyl; R⁸ and R⁹ are the same or different and are selected from the group consisting of hydrogen, lower alkyl, halo-lower alkyl, hydroxy-lower alkyl, methoxy-lower alkyl, amino-lower alkyl, lower alkoxycarbonyl, carboxy-lower alkyl, C₃–C₅-cycloalkyl, benzyl, acetyl, benzoyl, trifluoroacetyl, lower alkoxycarbonyl and benzyloxycarbonyl and l stands for an integer of 1 to 3, m is 1, n' is an integer of 1–4, o is an integer of 0 or 1, p an integer of 0–2, and q an integer of 0 or 1, the sum of o+p+q being 2; and n stands for an integer of 0–2, provided that R¹ is not ethyl when R⁵ is hydrogen.

6. An antibacterial composition comprising a carrier and, as an active ingredient, an antibacterially effective amount of the quinolone derivative or a pharmaceutically acceptable salt thereof according to claim 5.

* * * * *

UNITED STATES PATENT AND TRADEMARK OFFICE
CERTIFICATE OF CORRECTION

PATENT NO. : 5,153,203
DATED : October 6, 1992
INVENTOR(S) : Takashi YATSUNAMI, et al It is certified that error appears in the above-indentified patent and that said Letters Patent is hereby corrected as shown below:

Title page, Section [75] Inventors: Second inventors first name, "Hitodshi" should read -- Hitoshi --.

Column 2, line 27, "a lower group" should read -- a lower alkyl group --.

Column 2, line 37, " human being and " should read -- human beings and --.

Column 3, line 44, " Further, illustrative the " should read -- Further, illustrative of the --.

Column 3, line 53, " 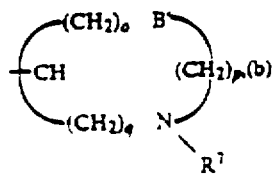 " should read

-- 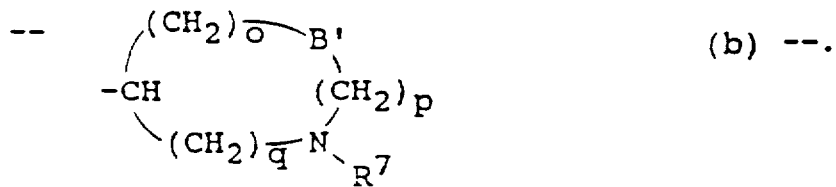 (b) --.

UNITED STATES PATENT AND TRADEMARK OFFICE
CERTIFICATE OF CORRECTION

PATENT NO. : 5,153,203
DATED : October 6, 1992
INVENTOR(S) : Takashi YATSUNAMI, et al It is certified that error appears in the above-identified patent and that said Letters Patent is hereby corrected as shown below:

Column 3, line 59, " 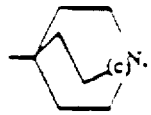 " should read

--  --.

Column 4, line 47, "aminolower" should read
-- amino-lower--.

Column 4, line 58, "-3oxazolidinyl" should read
-- -3-oxazolidinyl --.

Column 4, line 62, " -3oxazolidinyl " should read
-- -3-oxazolidinyl --.

Column 4, line 64, "-3oxazolidinyl" should read
-- -3-oxazolidinyl --.

UNITED STATES PATENT AND TRADEMARK OFFICE
CERTIFICATE OF CORRECTION

PATENT NO. : 5,153,203

DATED : October 6, 1992

INVENTOR(S) : Takashi YATSUNAMI, et al

It is certified that error appears in the above-indentified patent and that said Letters Patent is hereby corrected as shown below:

Column 5, line 29, " (tetrahydro1,3-oxazin) " should read -- (tetrahydro-1,3-oxazin) --

Column 5, line 40, " 5-(2-aminopropyl)(tetrahydro-1," should read -- 5-(2-aminopropyl)-(tetrahydro-1, --.

Column 5, line 41, " -(tetrahydro1,3-oxazin) " should read -- -(tetrahydro-1,3-oxazin) --.

Column 5, line 60, " -6-methylamiomethyl- " should read -- -6-methylaminomethyl- --.

Column 7, line 27, " known per as after " should read -- known per se after --.

Column 7, line 38, " carboxylprotecting " should read -- carboxyl-protecting --.

Column 9, line 7, " as y, " should read -- as Y, --.

Column 9, line 56, "compound[Id can" should read -- compound[Id] can --.

Column 9, line 57, "alkoxide [V with" should read -- alkoxide [V] with --.

UNITED STATES PATENT AND TRADEMARK OFFICE
CERTIFICATE OF CORRECTION

PATENT NO. : 5,153,203

DATED : October 6, 1992

INVENTOR(S) : Takashi YATSUNAMI, et al

It is certified that error appears in the above-identified patent and that said Letters Patent is hereby corrected as shown below:

Column 9, line 62, "compound [V may" should read
-- compound [V] may --.

Column 10, line 10, "above under." should read
Process 1

-- above under Process 1. --.

Column 10, line 15, "step sown" should read
-- step shown --.

Column 15, line 63, "3carboxylate" should read
-- 3-carboxylate --.

Column 16, line 50, "3carboxylate" should read
-- 3-carboxylate --.

Column 19, line 25, "3carboxylate" should read
-- 3-carboxylate --.

Column 20, line 9, "3hydroxypyrrolidine," should read
-- 3-hydroxypyrrolidine, --.

Column 23, lines 40-41, " columnchromatography" should read
--by column chromatography--.

UNITED STATES PATENT AND TRADEMARK OFFICE
CERTIFICATE OF CORRECTION

PATENT NO. : 5,153,203
DATED : October 6, 1992
INVENTOR(S) : Takashi YATSUNAMI, et al It is certified that error appears in the above-indentified patent and that said Letters Patent is hereby corrected as shown below:

Column 29, line 59, " -3-pyridinyloxy)" should read
    -- -3-pyrrolidinyloxy) --.

Column 34, line 60, "by columnchromatography" should read
    -- by column chromatography --.

Column 37, line 33, " chloroorm, " should read
    -- chloroform --.

Column 38, line 33, "by columnchromatography" should read
    -- by column chromatography --.

Column 41, line 36, "columnchromatography" should read
    -- column chromatography --.

Column 41, line 51, "columnchromatography" should read
    -- column chromatography --.

Column 42, line 60, "column-chromatography" should read
    -- column chromatography --.

Column 43, line 9, "column-chromatography" should read
    -- column chromatography --.

Column 44, line 3-4, "column-chromatography" should read
    -- column chromatography --.

UNITED STATES PATENT AND TRADEMARK OFFICE
CERTIFICATE OF CORRECTION

PATENT NO. : 5,153,203
DATED : October 6, 1992
INVENTOR(S) : Takashi YATSUNAMI, et al It is certified that error appears in the above-identified patent and that said Letters Patent is hereby corrected as shown below:

Column 44, line 13, "Cyclopropyl-6," should read
-- 1-Cyclopropyl-6, --.

Column 44, line 65, "alkanyloxy-lower" should read
-- alkanoyloxy-lower --.

Column 45, line 52, "$R^6$" should read --$R^5$--.

Signed and Sealed this

Fourth Day of January, 1994

BRUCE LEHMAN

Attest:

Attesting Officer    Commissioner of Patents and Trademarks